United States Patent
Cettina et al.

(10) Patent No.: US 11,224,544 B2
(45) Date of Patent: Jan. 18, 2022

(54) EXTENSIBLE DRESSINGS

(71) Applicant: Johnson & Johnson Consumer Inc., Skillman, NJ (US)

(72) Inventors: Melinda Cettina, Robbinsville, NJ (US); Paulo Oriani, Sao Paulo (BR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 406 days.

(21) Appl. No.: 16/129,720

(22) Filed: Sep. 12, 2018

(65) Prior Publication Data

US 2019/0099298 A1    Apr. 4, 2019

Related U.S. Application Data

(60) Provisional application No. 62/565,631, filed on Sep. 29, 2017.

(51) Int. Cl.

| *A61F 13/00* | (2006.01) |
|---|---|
| *A61F 13/02* | (2006.01) |
| *A61F 13/511* | (2006.01) |
| *D04H 1/728* | (2012.01) |

(52) U.S. Cl.
CPC .... *A61F 13/0206* (2013.01); *A61F 13/00029* (2013.01); *A61F 13/00038* (2013.01); *A61F 13/0226* (2013.01); *A61F 13/0243* (2013.01); *A61F 13/0246* (2013.01); *A61F 13/0259* (2013.01); *A61F 13/5116* (2013.01); *A61F 13/51121* (2013.01); *A61F 2013/00089* (2013.01); *A61F 2013/5113* (2013.01); *A61F 2013/51139* (2013.01); *A61F 2013/51143* (2013.01); *A61F 2013/51147* (2013.01); *A61F 2013/51178* (2013.01); *D04H 1/728* (2013.01)

(58) Field of Classification Search
CPC .......... A61F 13/00029; A61F 13/00038; A61F 13/0206; A61F 13/0226; A61F 13/0243; A61F 13/0246; A61F 13/0259; A61F 13/51121; A61F 13/5116; A61F 2013/00089; A61F 2013/51139; A61F 2013/51143; A61F 2013/51147; A61F 2013/51178; D04H 1/728

See application file for complete search history.

(56) References Cited

U.S. PATENT DOCUMENTS

| 810,131 | A | * | 1/1906 | Green | ............... A61F 13/15203 |
|---|---|---|---|---|---|
| | | | | | 604/378 |
| RE24,906 | E | | 12/1960 | Ulrich | |
| 3,029,819 | A | * | 4/1962 | Ernest | ....................... A61F 2/06 |
| | | | | | 623/1.51 |

(Continued)

FOREIGN PATENT DOCUMENTS

| CN | 201939586 U | 8/2011 |
|---|---|---|
| CN | 105997348 A | 10/2016 |

(Continued)

OTHER PUBLICATIONS

European Search Report; Appln. No. 18197746.3-1102; dated Feb. 28, 2019.

*Primary Examiner* — Camtu T Nguyen

(57) ABSTRACT

The present invention relates to dressings such as bandages or tapes improved extensibility. The present invention further relates to dressings such as bandages or tapes which are extensible so as to at least partially conform to a body contour at wound surface upon stretching of the dressing.

19 Claims, 13 Drawing Sheets

(56) References Cited

U.S. PATENT DOCUMENTS

| | | |
|---|---|---|
| 3,389,827 A | 6/1968 | Abere et al. |
| 3,525,337 A | 8/1970 | Simons et al. |
| 3,653,382 A | 4/1972 | Easley et al. |
| 4,112,213 A | 9/1978 | Waldman |
| 4,310,509 A | 1/1982 | Berglund et al. |
| 4,323,557 A | 4/1982 | Rosso et al. |
| 4,472,480 A | 9/1984 | Olson |
| 4,606,338 A | 8/1986 | Greenway et al. |
| 4,737,410 A | 4/1988 | Kantner |
| 5,576,090 A | 11/1996 | Suzuki |
| 5,906,879 A | 5/1999 | Huntoon et al. |
| 6,838,589 B2 | 1/2005 | Liedtke et al. |
| 7,030,288 B2 | 4/2006 | Liedtke et al. |
| 7,612,248 B2 | 11/2009 | Burton et al. |
| 8,500,704 B2 * | 8/2013 | Boehringer ............. A61F 13/36 604/313 |
| 9,445,951 B2 | 9/2016 | Moberg-Alehammar et al. |
| 2010/0100023 A1 * | 4/2010 | Johnson .................. A61F 13/00 602/48 |
| 2011/0092872 A1 | 4/2011 | Christiansen |
| 2013/0282049 A1 | 10/2013 | Peterson et al. |
| 2014/0234575 A1 | 8/2014 | Mitsuno et al. |
| 2014/0308867 A1 | 10/2014 | Van Emmerick et al. |
| 2016/0067940 A1 | 3/2016 | Liebe et al. |
| 2017/0196734 A1 | 7/2017 | Keinan et al. |

FOREIGN PATENT DOCUMENTS

| | | |
|---|---|---|
| GB | 2 188 241 A | 9/1987 |
| WO | WO 1998/02610 | 1/1998 |
| WO | WO 2000/36199 A | 6/2000 |
| WO | WO 2000/051650 A | 9/2000 |
| WO | WO 2003/063746 A | 8/2003 |
| WO | WO 2016/040613 A | 3/2016 |

* cited by examiner

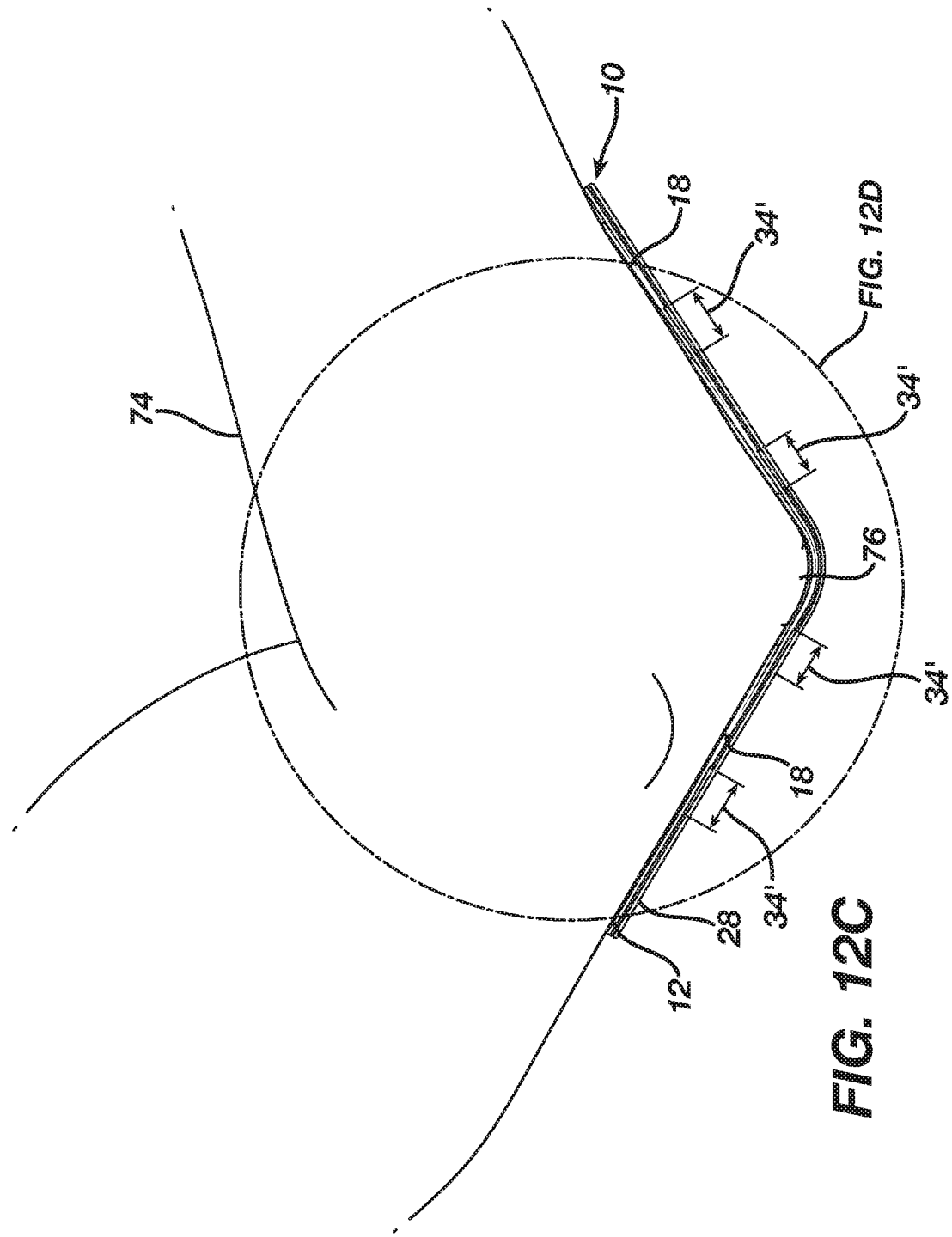

EXTENSIBLE DRESSINGS

CROSS-REFERENCE TO RELATED APPLICATION

The present application claims the benefit of the earlier filing date of U.S. provisional patent application 62/565,631 filed Sep. 29, 2017, the entirety of which application is hereby incorporated by reference herein as if fully set forth herein.

FIELD OF THE INVENTION

The present invention relates to dressings such as bandages or tapes improved extensibility. The present invention further relates to dressings such as bandages or tapes which are extensible so as to at least partially conform to a body contour at wound surface upon stretching of the dressing.

BACKGROUND OF THE INVENTION

Dressings such as bandages and tapes for applying to and/or covering the skin have been known for some time. Such dressings have gained wide acceptance for closing minor wounds, protecting minor wounds and/or covering abrasions. In some instances, microporous or breathable, bandages or tapes have been developed and are used either to cover minor wounds (including wounds that have been partially healed).

While such dressings have been greatly improved over the years in that, for example, they have incorporated microporous materials allowing the wound to breath and permitting water vapor to escape from the wound, hence, reducing chances of wound maceration, there remains a need for dressings which improves extensibility and which, optionally, to yield to at least partially conform to the contour of the body of the user in response to a movement of the skin surface at a site of a wound. Accordingly, in order for a dressing to provide the aforementioned attributes, the dressing comprises a wound dressing assembly providing improved extensibility, comprising a layer of resilient material and a backing layer attached to the layer of resilient material by discrete adhesive regions disposed on a surface of the layer of resilient material at discrete areas thereof.

It is, therefore, an aspect of the present invention to provide dressings that may be used to cover, protect wounds and facilitate wound healing. It is also an aspect of the present invention to provide a wound dressing assembly comprising a layer of resilient material and a backing layer both having improved elongation. It is also an aspect of the present invention to provide a wound dressing assembly comprising a layer of resilient material and a backing layer, wherein the layer of resilient material is longitudinally extendable x upon stretching of any backing layer attached thereto. It is a further aspect of the present invention to provide a wound dressing assembly comprising a layer of resilient material and a backing layer attached to the layer of resilient material by discrete adhesive regions disposed on a surface of the layer of resilient material at discrete areas thereof. Other aspects of the present invention will be readily apparent from the ensuing description and claims.

SUMMARY OF THE INVENTION

The present invention relates to A dressing comprising a layer of resilient material, the layer of resilient material having a length direction (LD) and a width direction (WD), which together define a horizontal plane (HP), the horizontal plane HP having a first surface and a second opposed surface, a longitudinal centerline (LC) and a transverse centerline (TC), the layer of resilient material further including one or more pleats formed in at least a portion thereof, each pleat comprising two or more folds, at least one of which folds each pleat shares in common with a neighboring pleat when there are two or more pleats, each pleat further has a length extending in a direction taken along the pleat length, a pleat width, and a lengthwise centerline (PC) bisecting the pleat width, wherein the direction of each pleat length independently makes an angle φ with the longitudinal centerline LC in the horizontal plane HP, and wherein the angle φ has a value that falls within a range specified by the equation: $0° < \varphi < 180°$.

The present invention further relates to a dressing comprising a layer of resilient material, the layer of resilient material having:

(a) a length direction (LD) and a width direction (WD), which together define a horizontal plane (HP), the horizontal plane HP having a first surface and a second opposed surface, a longitudinal centerline (LC) and a transverse centerline (TC);

(b) one or more pleats formed in at least a portion of the layer of resilient material, each pleat comprising two or more folds, at least one of which folds each pleat shares in common with a neighboring pleat, each pleat further has a pleat length extending in a pleat direction, a pleat width, and a lengthwise centerline (PC) bisecting the pleat width, wherein each pleat direction of a pleat length independently makes an angle φ with the longitudinal centerline LC in the horizontal plane HP, and wherein the angle φ0 has a value that falls within a range specified by the equation: $0° < \varphi < 180°$;

(c) a plurality of discrete adhesive regions disposed on the second surface of the layer of resilient material at discrete areas of the layer of resilient material; and (d) an additional layer of material having a first surface and a second opposed surface, the first surface of the additional layer of material adhered to the second surface of the layer of resilient material by the plurality of discrete adhesive regions.

The present invention still further relates to a dressing comprising a layer of resilient material, the layer of resilient material having:

(i) a first longitudinal edge and a second longitudinal edge, which together define a width (W) of the layer of resilient material;

(ii) a first transverse edge and a second transverse edge, which together define a length (L) of the layer of resilient material, the length L and width W of the layer of resilient material 12 having a length direction (LD) and a width direction (WD) respectively, the length direction LD and the width direction WD together defining a horizontal plane (HP), the horizontal plane HP having a first surface and a second opposed surface, a longitudinal centerline (LC), and a transverse centerline (TC); and (iii) a plurality of pleats formed in at least a portion of the layer of resilient material, each pleat comprising a multiplicity of folds, each fold extending from the first longitudinal edge to the second longitudinal edge, each pleat having a closed end (or an apex) 36 defined by a fold, an open end spaced from and opposite the closed end (or apex), and a trailing side wall and an opposing leading side wall sharing a common transverse edge running along the fold of the closed end (the apex) of the pleat, each of the trailing and leading side walls of the pleat further has a second transverse edge spaced from and opposite the common transverse edge and disposed on opposite sides of the open end of the pleat, wherein at least two (adjacent) neighboring pleats are arranged in a spaced relation to each other with a substantially fold-free segment of the layer of resilient material spanning the distance from the second transverse edge of the leading side wall of one of the pleats to the second transverse edge of the trailing sidewall of the neighboring pleat.

BRIEF DESCRIPTION OF THE DRAWINGS

An embodiment of this invention will now be described in greater detail, by way of illustration only, with reference to the accompanying drawings, in which:

FIG. 12C shows a side view of an exemplary embodiment of the dressing and elbow joint of FIG. 12A with the elbow joint in a flexed configuration.

DETAILED DESCRIPTION OF THE INVENTION

Figure 1A:
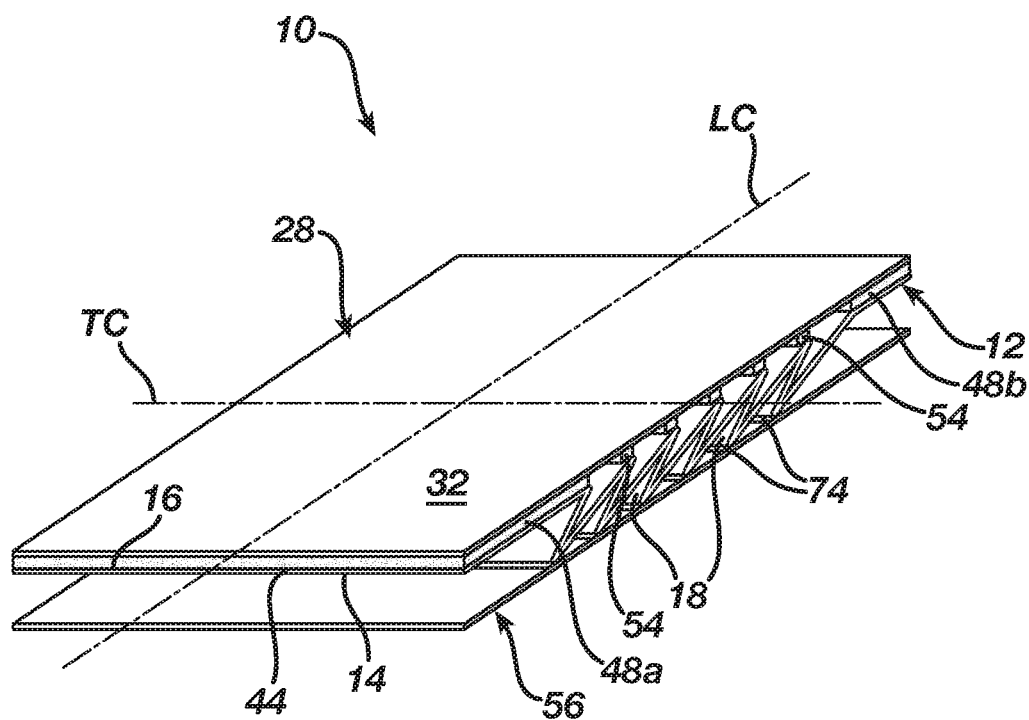
FIG. 1A shows a perspective view of a dressing in according with an exemplary embodiment of the present invention.

The dressing of the present invention can comprise, consist of, or consist essentially of the essential elements and limitations of the invention described herein, as well any of the additional or optional features, components, or limitations described herein.

The term "comprising" (and its grammatical variations) as used herein is used in the inclusive sense of (and, interchangeably with the terms) "having" or "including" and not in the exclusive sense of "consisting only of" The terms "a" and "the" as used herein are understood to encompass the plural as well as the singular.

As used herein, terms "skin" and "tissue" are interchangeable and refer to mammalian skin.

All documents incorporated herein by reference, by portion or in their entirety, are only incorporated herein to the extent that they are not inconsistent with this specification.

In certain embodiments, the present invention as disclosed herein may be practiced in the absence of any component, element (or group of components or elements) or method step which is not specifically disclosed herein.

Referring to the drawings in detail, wherein like reference numerals indicate like elements throughout, there is shown in FIGS. 1A-8C, a dressing, generally designated by the reference numeral 10, in accordance with an exemplary embodiment of the present invention.

Pleated Layer of Resilient Material

Figure 1B:
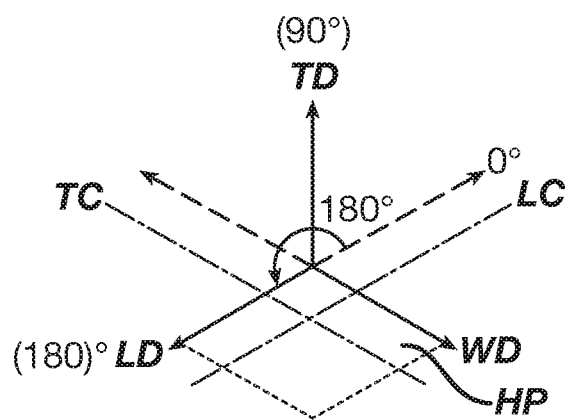
FIG. 1B shows a perspective view of the coordinate system, including axes LD, WD, TD in relation to the horizontal plane HP of a layer of resilient material in accordance with an exemplary embodiment of the present invention.

As illustrated in FIG. 1A, a dressing 10 in accordance with an exemplary embodiment of the present invention comprises a layer of resilient material 12 having a first surface 14 and second surface 16, opposing the first surface 14, the surfaces 14, 16 extending in a length direction (LD) and a width direction (WD) (see FIGS. 1A-2C), which directions define a horizontal plane (HP). FIG. 1B shows how the length direction (LD) and the width direction (WD)

of the surface of the layer of resilient material 12 together define the horizontal plane (HP). The first surface 14 and the second opposed surface 16 of the layer of resilient material 12 include the same longitudinal centerline (LC) extending in the length direction (LD) and a transverse centerline (TC) extending in the width direction (WD) as shown with respect to dressing 10 in FIGS. 1A and 1B.

In certain embodiments, the layer of resilient material 12 is formed from any suitable nonwoven fabrics, including, but not limited to, spunlace, spunbond, thermo bond, wetlaid nonwoven fabrics. Spunlace nonwovens are typically made using a mechanical bonding process (spun-lacing method) which employs jets of water to entangle fibers, deposition of the entangled fibers onto a collecting belt in a uniform random manner, followed by bonding of the entangled fibers. and thereby provide fabric integrity. Any suitable synthetic fibers can be used to produce spunlace nonwoven fabrics, including polypropylene, polyethylene, polyethylene terephthalate, nylon, and the like.

Thermal bonded nonwovens are fabrics produced by using heat to melt thermoplastic powders or fibers, including polyester, polypropylene, and polyethylene terephthalate fibers. Typically, the thermal bonding process begins by taking a thermoplastic fiber or a blend of thermoplastic fibers and forming them into a fiber batt, using air-laying machines, for example. The resulting fibrous webs are then heated using various thermal bonding methods, including through-air bonding and ultrasonic energy bonding.

Wetlaid nonwovens are typically produced in a process similar to paper making in which a nonwoven web is produced by filtering an aqueous suspension of fiber onto a screen conveyor belt or perforated drum. Many wet laid nonwovens are made with wood pulp or other natural fibers blended with synthetic fibers.

Figure 2A:
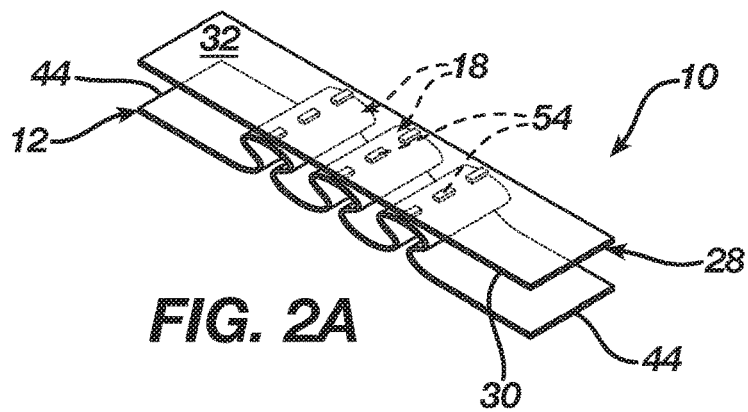
FIG. 2A shows a top perspective view of a dressing including a layer of resilient material having a plurality of pleats formed therein and an additional layer of material adhered to the layer of resilient material.
Figure 2B:
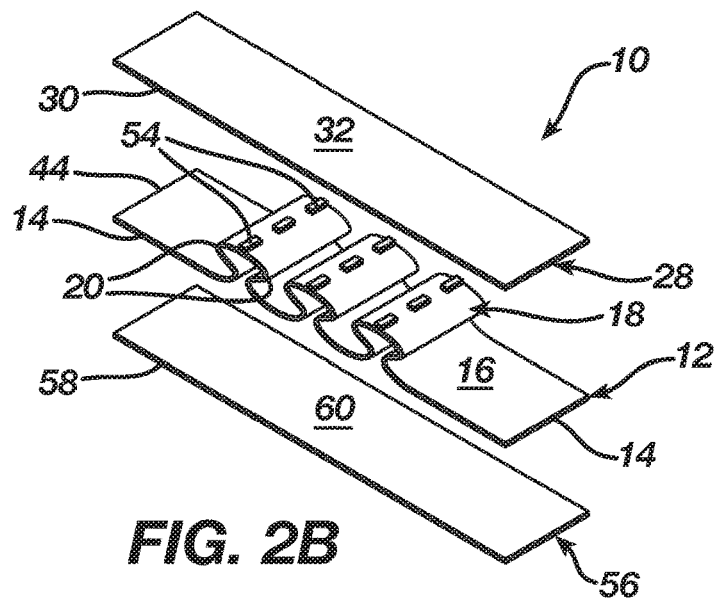
FIG. 2B shows an exploded view of the dressing of FIG. 2A further including a release liner disposed on the face of the layer of resilient material opposite to the face on which is disposed the additional layer of material.
Figure 2C:
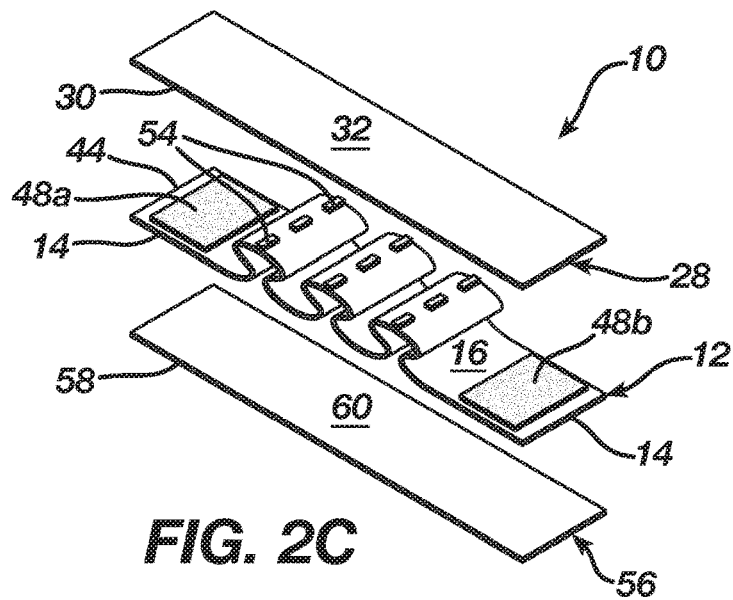
FIG. 2C shows an exploded view of the dressing of FIG. 2B further including discrete adhesive regions disposed proximate to each of the transverse edges of the layer of resilient material.
Figure 3A:
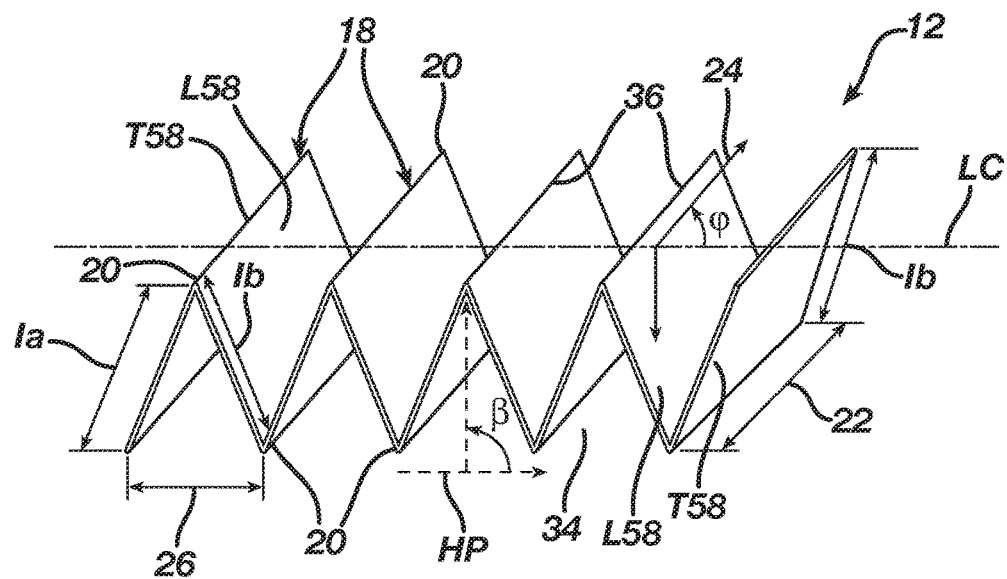
FIG. 3A shows a perspective view of an exemplary embodiment of the layer of resilient material in accordance with the present invention, showing a coordinate system located on a pleat on the layer of resilient material to illustrate angles φ and β.

As illustrated in FIGS. 1A, and 3A an exemplary embodiment of the layer of resilient material 12 comprises a plurality of pleats 18, each pleat comprising folds 20 such that when two or more contiguous pleats 18 are formed in the layer of resilient material 12 each pleat 18 shares two or more of which folds 20 in common with a neighboring pleat 18. A number of different types of pleats 18 are known in the art. Examples of pleated structures useful in the current invention include, but are not limited to, those shown in FIGS. 2A-7, 9A, and 9B.

Pleats may be incorporated into the layer of resilient material 12 by any suitable methods known in the art, including by a mechanical folding, for example.

Figure 7:
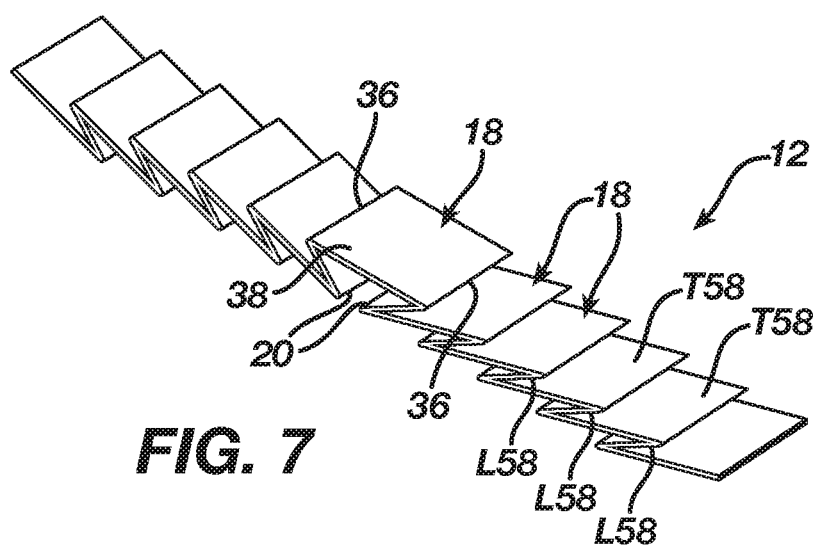
FIG. 7 shows a top perspective view of another exemplary embodiment of the layer of resilient material including different types of pleats formed therein.

FIG. 6A, for example, shows a layer of resilient material 12 having one or more pleats 18, each of which pleats 18 having two or more folds 20, which can be rounded folds as shown in FIG. 6A or creased folds 20 as shown in FIG. 7. In one embodiment, as shown in FIG. 6A, each pleat 18 includes rounded folds 20, at least one of which rounded folds 20 is shared in common between two neighboring pleats 18. Each pleat 18 of the layer of resilient material 12 in FIG. 6A includes a pleat length 22, the pleat length 22 extending in a pleat direction 24. Each pleat direction 24 of a pleat length 22 independently makes an angle φ with the longitudinal centerline LC in the horizontal plane HP of the layer of resilient material 12. In FIG. 6A, pleat direction 24 of a pleat length 22 is shown as making an angle φ, with the longitudinal centerline LC (not shown), wherein φ is about 90°. However, the angle φ can have a range of values specified by the equation: $0°<\varphi<180°$, optionally from $30°<\varphi<150°$, or optionally from $40°<\varphi<140°$. As such, FIG. 6B illustrates a top view of an exemplary layer of resilient material 12 having two or more pleats 18, each having a pleat length 22 extending in a pleat direction 24, the pleat direction 24 making an angle φ with the longitudinal centerline LC of the layer of resilient material 12, wherein, angle φ has a non-zero value less than 90°, for example, about 60°, about 45°, or about 30°.

Figure 3B:
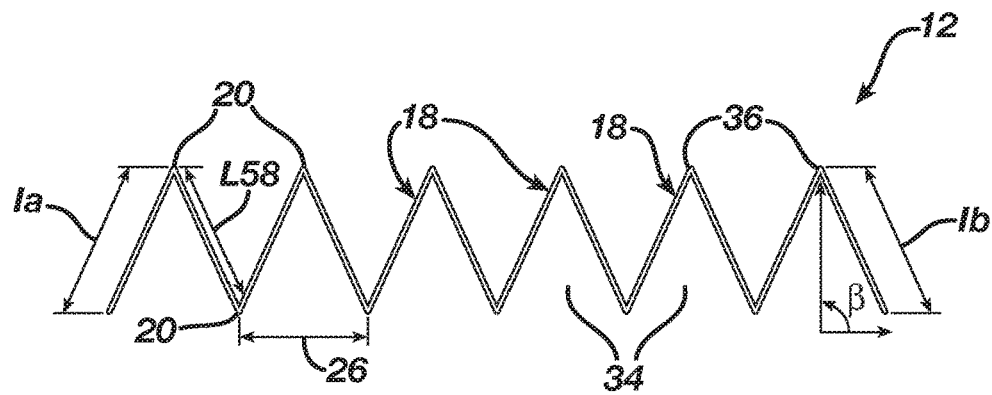
FIG. 3B shows a side view of the exemplary embodiment of the layer of resilient material of the invention illustrated in FIG. 3A.
Figure 4:
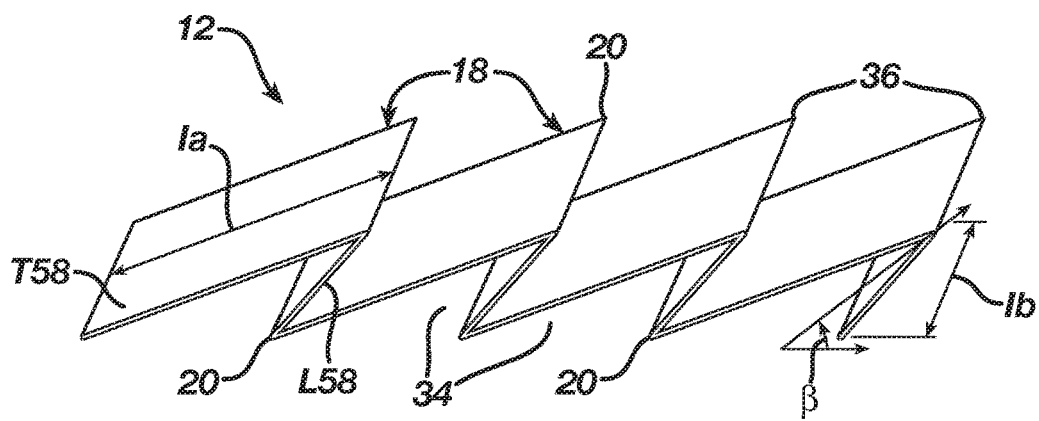
FIG. 4 shows a perspective view of another exemplary embodiment of the layer of resilient material in accordance with the present invention.

In one embodiment, as shown in FIGS. 3A and 3B, a layer of material 12 has one or more pleats 18, each of which pleats 18 including two or more folds 20. Unlike the pleats of the embodiment of FIG. 6A, the pleats of the embodiment of FIGS. 3A and 3B have creased (e.g., sharp or angled) folds 20, each "crease" of the creased fold 20 defining a crown 36. In one embodiment, each pleat 18 includes creased folds 20, at least one of which creased folds 20 is shared in common between two neighboring pleats 18. Each pleat 18 of the layer of resilient material 12 in FIG. 3A includes a pleat length 22, and extends in a pleat direction 24. Each pleat direction 24 of a pleat length 22 independently makes an angle φ with the longitudinal centerline LC (not shown) in the horizontal plane HP of the layer of resilient material 12. In FIG. 3A, pleat direction 24 of a pleat length 22 is shown as making an angle φ, wherein angle φ is about 90°, with the longitudinal centerline LC of the layer of resilient material 12. However, the angle φ can have a range of values specified by the equation: $0°<\varphi<180°$, optionally from $30°<\varphi<150°$, or optionally from $40°<\varphi<140°$. In one embodiment, each pleat 18, in FIG. 3A, includes one creased fold defining a crown 36 of the pleat 18, one or two creased folds 20, each of which define a root (i.e., the fold 20 [creased or non-creased] furthest away from the skin surface of a user and, accordingly, as the case may be, closest to the additional layer of material 28) of the pleat 18, and a pair of legs (or side walls) L58 and T58 defining pleat 18 sidewalls, the pair of legs (or side walls) L58 and T58 of each pleat 18 being joined to one another at the crown 36 of the pleat 18, i.e. share a common fold 20 at the crown 36 of the pleat 18. In one embodiment, each of the side walls L58 and T58 of a pleat 18 shares a common fold 20 with a side wall L58 or a side wall T58 of a neighboring pleat 18 (i.e. at the root of the neighboring pleat 18). In one embodiment, each pleat 18, includes one or two creased folds 20, each of which define a root of the pleat 18, and a pair of legs (or side walls) L58 and T58 defining pleat 18 sidewalls, wherein the leading pleat leg (or side wall) L58 has a length lb and the trailing pleat 18 leg (or side wall) T58 has a length la. In one embodiment, as shown in FIGS. 3A and 3B, the leading pleat leg (or side wall) L58 of any pleat 18 has a length lb and the trailing pleat leg (or side wall) T58 of the same pleat 18 has a length la, wherein the length lb and the length la are substantially equal. The leading pleat 18 leg (or side wall) L58 of any pleat 18 can be longer than, shorter than, or the same length as the trailing pleat 18 leg (or side wall) T58 of the same pleat 18. As such, in one embodiment, as shown in FIG. 4, the layer of resilient material 12 includes pleats 18, each pleat 18 including a trailing pleat leg (or side wall) T58 and a leading pleat leg (side wall) L58, wherein the trailing pleat leg (or side wall) T58 is longer than the leading pleat leg (or side wall) L58, i.e., la> lb.

In one embodiment, a dressing 10 of the present invention includes a layer of resilient material 12, as illustrated in FIGS. 3A and 3B, including one or more pleats 18, each of which pleats 18 includes the two or more folds 20 incorporated to form an open end 34 (i.e., as in the "open" portion of a "V" or "L") and a closed end 36 (i.e., as in the angled corner opposite the "open" portion of such "V" or "L"), with a pair of side walls (i.e., leading side wall L58 and trailing side wall T58) of the pleat 18, each side wall extending between a fold 20 contributing to formation of an open end 34 and the closed end 36. In one embodiment of the pleats 18 of the layer of resilient material 12 the leading side wall L58 and trailing side wall T58 of a pleat 18 share a common transverse edge 70A at the closed end 36 of the pleat 18.

Figure 5A:
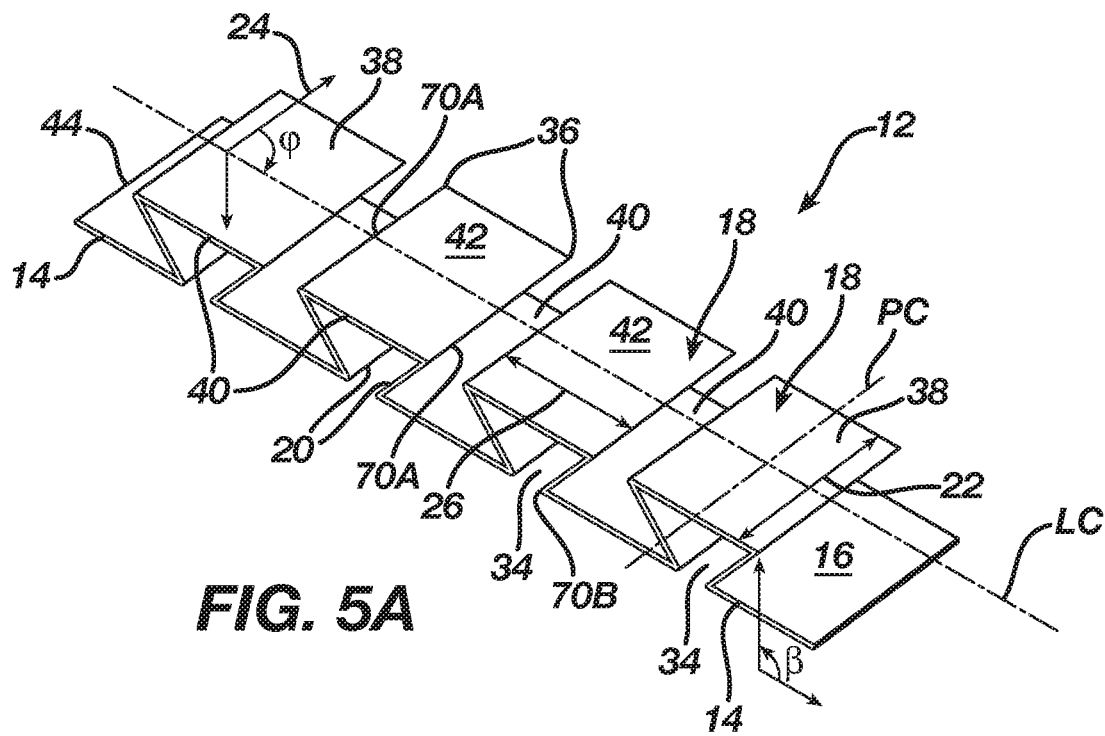
FIG. 5A shows a perspective view of another exemplary embodiment of the layer of resilient material in accordance with the present invention.
Figure 5B:
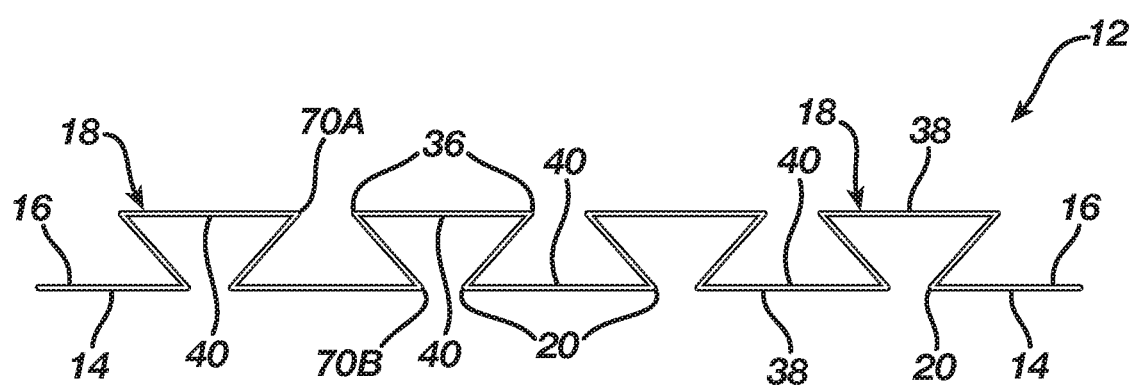
FIG. 5B shows a side view of the exemplary embodiment of the layer of resilient material in FIG. 5A.
Figure 6:
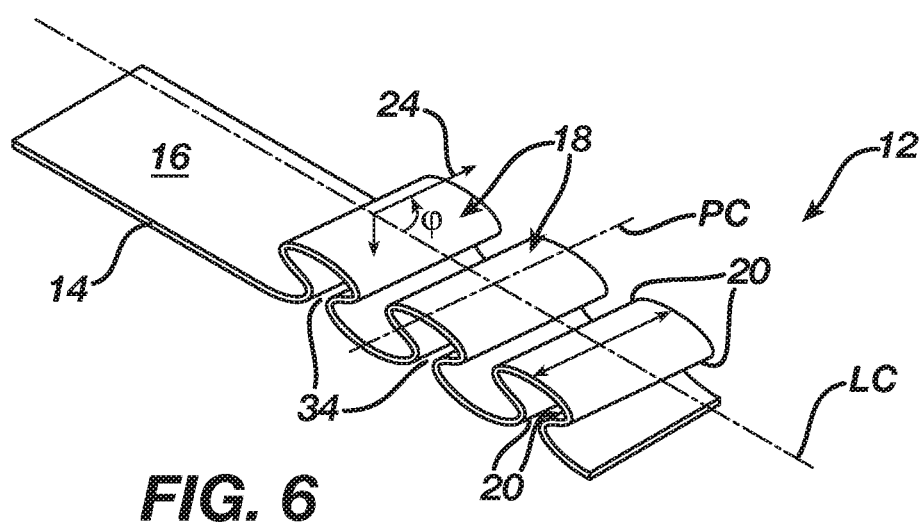
FIG. 6 shows a top perspective view of another exemplary embodiment of the layer of resilient material in accordance with the present invention.

In one embodiment of the layer of resilient material 12, such as in FIGS. 5A and 5B, each of the leading side wall L58 and trailing side wall T58 of a pleat 18 has a transverse edge (or pleat line) 70A at a different closed end 36 of the pleat 18.

In one embodiment of the layer of resilient material 12, any pleat 18 is resiliently structurally biased (or, has a mechanical tendency for positioning) toward substantially overlying a leading side wall L58 (or a trailing sidewall T58) of an adjacent pleat 18 or it is structurally biased toward overlaying an adjacent segment 72 of the layer of resilient material 12 interposed between the pleat 18 and a neighboring pleat 18.

In one embodiment, as shown in FIGS. 3A and 3B, the layer of resilient material 12, one or more of the pleats 18 has open end 34 and a closed end 36 and a pair of side walls (i.e., leading side wall L58 and trailing side wall T58), each side wall extending between a fold 20 contributing to formation of the open end 34 and the closed end 36, the one or more pleats 18 being resiliently structurally biased axially (or, has a mechanical tendency for maintaining positioning) at an angle β with the horizontal plane HP of the layer of resilient material 12. In one embodiment of the layer of resilient material 12, one or more of the pleats 18 has an open end 34 and a closed end 36 and a pair of side walls (i.e., leading side wall L58 and trailing side wall T58), each side wall extending between a fold 20 contributing to formation of the open end 34 and the closed end 36, the one or more pleats 18 being resiliently biased axially at an angle β with the horizontal plane HP of the layer of resilient material 12, wherein the angle β, can have any value that falls within a range specified by the equation: $0°≤β≤180°$, optionally, $0°≤β≤5°$ (or, $175°≤β≤180°$. As such, in one embodiment of the layer of resilient material 12, as illustrated in FIG. 4, a pleat 18 has an open end 34 and a closed end 36 and a pair of side walls (i.e., leading side wall L58 and trailing side wall T58), each side wall extending between a fold 20 contributing to formation of the open end 34 and the closed end 36, wherein the pleat 18 is resiliently biased axially at an acute angle β with the horizontal plane HP of the layer of resilient material 12.

In another embodiment of the dressing 10 in accordance with the present invention, the dressing 10 includes a layer of resilient material 12, as illustrated in FIGS. 5A and 5B, which includes one or more pleats 18, each of which has folds 20 are arranged such that each pleat 18 has a pair of adjacent (i.e., near, or next to, each other without necessarily touching) closed ends 36, substantially laterally spaced apart by a substantially fold-free segment 38 of the layer of resilient material 12. As used herein, the term "substantially fold free" further means "fold-free" or "without any folds whatsoever". In one embodiment, the layer of resilient material 12 includes one or more pleats 18, each of which has folds 20 are arranged such that each pleat 18 has a pair of adjacent closed ends 36, substantially laterally spaced apart by a substantially fold-free segment 38 of the layer of resilient material 12, wherein each of the substantially fold-free segments 38 has an inner surface 40 and an opposed outer surface 42, and wherein the inner surface 40 of a substantially fold-free segment 38 of any pleat 18 faces in a direction opposite to the direction of an inner surface 40 of a substantially fold-free segment 38 of an adjacent pleat 18. As illustrated in FIG. 5A, each pleat 18 has a pleat length 22 extending in pleat direction 24, and a lengthwise centerline of PC bisecting the substantially fold-free segment 38. Each pleat direction 24 of a pleat length 22 independently makes an angle φ with the longitudinal centerline LC (not shown) in the horizontal plane HP of the layer of resilient material 12. In FIG. 5A, pleat direction 24 of a pleat length 22 is shown as making an angle φ, wherein angle φ is about 90°, with the longitudinal center line LC of the layer of resilient material 12. However, pleat lengths 22 of pleats 18 can be oriented to make any angle φ with the longitudinal center line LC such that the angle φ can have any value in the range of values specified by the equation: $0°<φ<180°$, optionally $30°<φ<150°$, or optionally from $40°<φ<140°$.

In one embodiment, a dressing 10 of the present invention includes a layer of material 12, as shown in FIG. 7, which has one or more pleats 18 of different types of pleats 18. As shown in FIG. 7, the layer of resilient material 12 includes at least one pleat 18 including folds 20 arranged such that the at least one pleat 18 includes a pair of adjacent closed ends 36, substantially laterally spaced apart by a substantially fold-free segment 38 of the layer of resilient material 12. In one such embodiment, each of the remaining pleats 18 to each side of the at least one pleat 18 with the pair of adjacent closed ends 36, has folds 20 arranged such that each pleat 18 only has one closed end 36.

In one embodiment, a dressing 10 of the present invention includes a layer of resilient material 12, as illustrated in FIGS. 4 and 7, which includes one or more pleats 18, each of which pleats 18 includes the two or more folds 20 arranged such that includes one creased fold defining a crown 36 of the pleat 18 (reference numeral 36), opposing one or two creased folds 20, each of which defines a root of the pleat 18, and a pair of legs L58 and T58 (i.e., leading side wall L58 and trailing side wall T58) each of which extends between a crown 36 and a root (an opposing fold) of the pleat 18 and wherein the pair of legs L58 and T58 of each pleat 18 are axially oriented such that a leading leg L58 of a pleat 18 at least partially overlaps a trailing leg T58 of an adjacent pleat 18 or a segment of the layer of resilient material 12

Figure 9A:
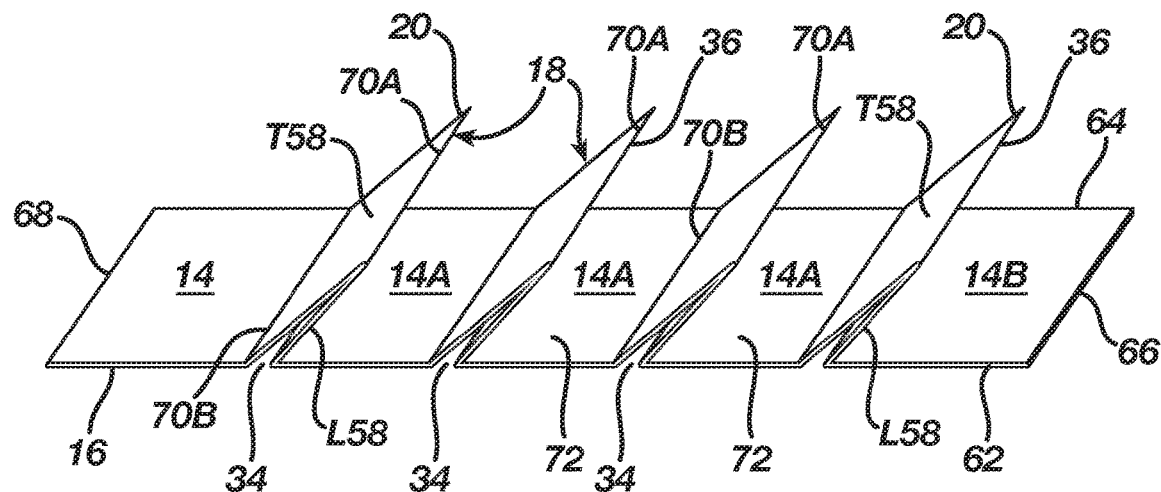
FIG. 9A shows a top perspective view of an exemplary embodiment of the layer of resilient material having pleats in accordance with the present invention.
Figure 9B:
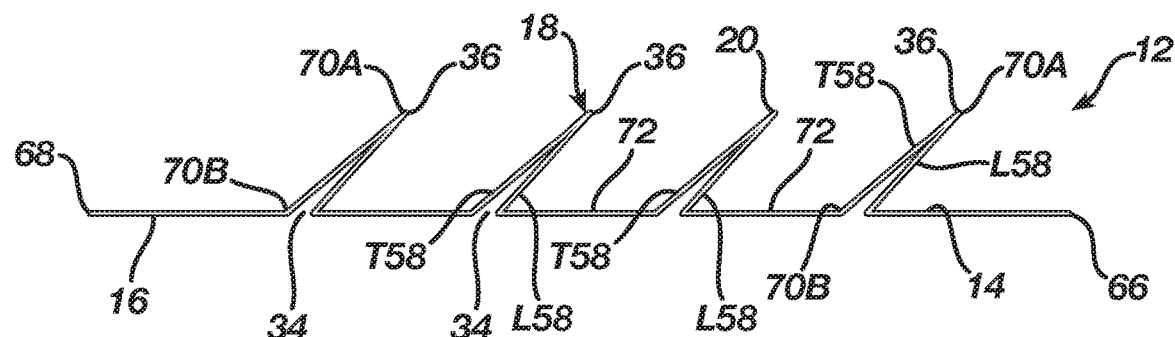
FIG. 9B shows a side view of the exemplary embodiment in accordance with FIG. 9A.

In one embodiment, a dressing 10 comprises a layer of resilient material 12, as shown in FIGS. 9A and 9B, the layer of resilient material 12 includes: (i) a first longitudinal edge (62) and a second longitudinal edge (64), which together define a width (W) of the layer of resilient material 12; and (ii) a first transverse edge (66) and a second transverse edge (68), which together define a length (L) of the layer of resilient material 12, the length L and width W of the layer of resilient material 12 having a length direction (LD) and a width direction (WD) respectively, the length direction LD and the width direction WD together defining a horizontal plane (HP), the layer of resilient material 12 having a first surface 14 and a second opposed surface 16, a longitudinal centerline (LC), not shown, and a transverse centerline (TC), also not shown. In one embodiment, the layer of resilient material 12, as shown in FIGS. 9A and 9B, includes a plurality of pleats 18 formed in at least a portion of the layer of resilient material 12, each pleat 18 comprising a multiplicity of folds 20, each fold 20 extending from the first longitudinal edge 62 to the second longitudinal edge 64 of the layer of resilient material 12, each pleat 18 having a closed end (or an apex) 36 defined by a fold 20, an open end 34 spaced from and opposite the closed end (or apex) 36, and a pair of opposing side walls, T58 and L58 respectively. In one such embodiment, the pair of opposing side walls T58 and L58 of a pleat 18 share a common transverse edge 70A defined by the fold 20 at the closed end (or apex) 36 of the pleat 18, each of the side walls T58 and L58 extending between the common transverse edge 70A and the open end 34 of the pleat 18, and wherein each of the side walls T58 and L58 further includes a second transverse edge 70B opposite the common transverse edge 70A and defined by a fold 20 at or proximate the open end 34 of the pleat 18. In one embodiment, as shown in FIGS. 9A and 9B, the layer of resilient material 12 includes a plurality of pleats 18, at least two of which are arranged in a spaced relation to each other with a substantially fold-free segment 72 of the layer of resilient material 12 extending from the second transverse edge 70B of the side wall L58 of one of the pleats 18 to the second transverse edge 70B of the sidewall TL58 of the other pleat 18. In one embodiment, as illustrated in FIGS. 1A, and 2A-2C, the dressing 10 in accordance with an exemplary embodiment of the present invention further includes an additional layer of material 28 attached to the layer of resilient material 12. Any suitable method of attaching the additional layer of material 28 to the layer of resilient material 12 may be used, including using an adhesive. The additional layer of material 28 can be in the form of a single layer or multiple layers and may be incorporated to act as a protective backing layer for the layer of resilient material 12. When used as a backing layer, additional layer of material 28 may, in addition to the rectangular shape illustrated in FIGS. 1A, and 2A-2C, have various other shapes, including but not limited to, circular, oval, ovoid, or oblong etc. In such an embodiment, the shape of the bandage and tape 10 may be defined by the shape of additional layer of material 28. In some such embodiments, additional layer of material 28 may be thin, highly flexible or deformable, water-impervious, and clear or opaque. Generally, in some such embodiments, the thickness of additional layer of material 28 is between about 0.05 to 0.2 millimeter ("mm") to achieve the forming and flexing characteristics desired.

Figure 10A:
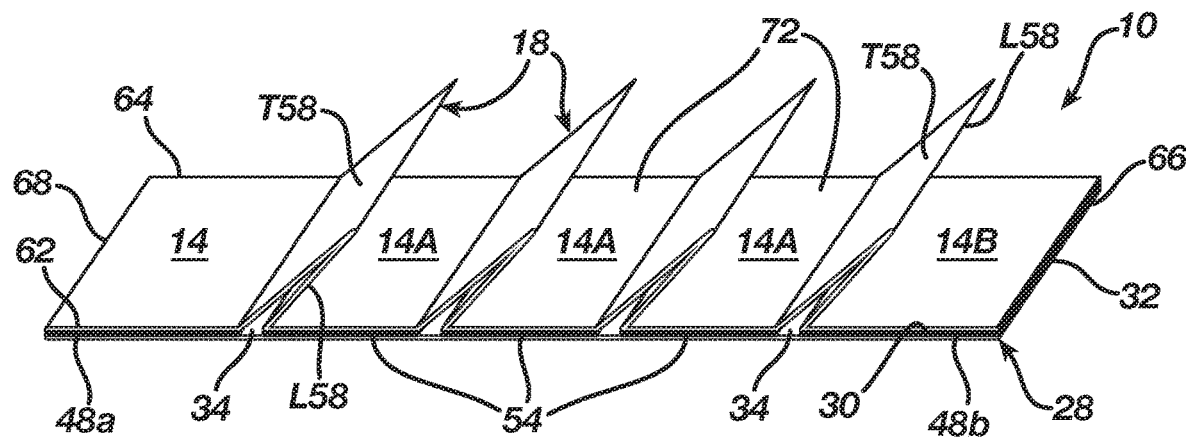
FIG. 10A shows a top perspective view of an exemplary embodiment of the dressing in accordance with the present invention.
Figure 10B:
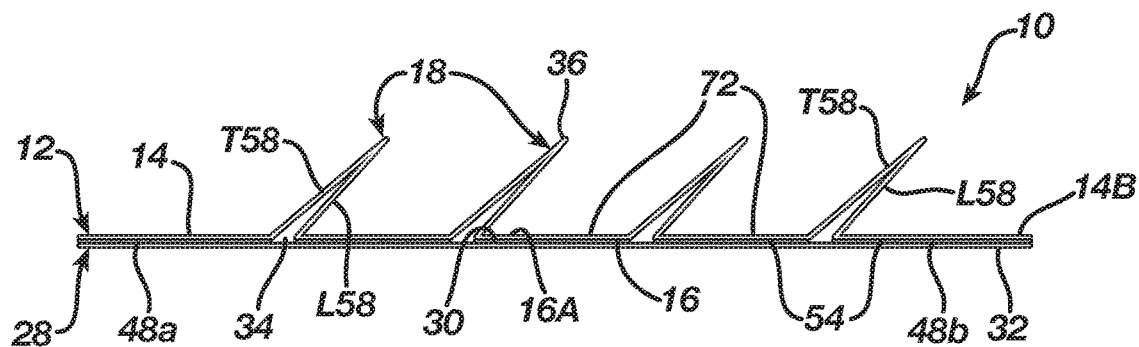
FIG. 10B shows a side view of the exemplary embodiment of the dressing illustrated in FIG. 10A.

In one embodiment, a dressing 10 comprises a layer of resilient material 12, as shown in FIGS. 10A and 10B, which includes a plurality of pleats 18, at least two of which are arranged in a spaced relation to each other with a substantially fold-free segment 72 of the layer of resilient material 12 extending from a second transverse edge 70B of a side wall L58 of one of the pleats 18 to a second transverse edge 70B of a sidewall TL58 of the other pleat 18. In one embodiment of the dressing 10, as shown in FIGS. 10A and 10B, the substantially fold-free segment 72 between a pair of neighboring pleats 18 has a surface 14A. In one embodiment of the dressing 10, as shown in FIGS. 10A and 10B, a substantially fold-free segment 72 between a pleat 18 and a transverse edge (66 or 68) of the layer of resilient material 12 has a surface 14B.

Figure 11A:
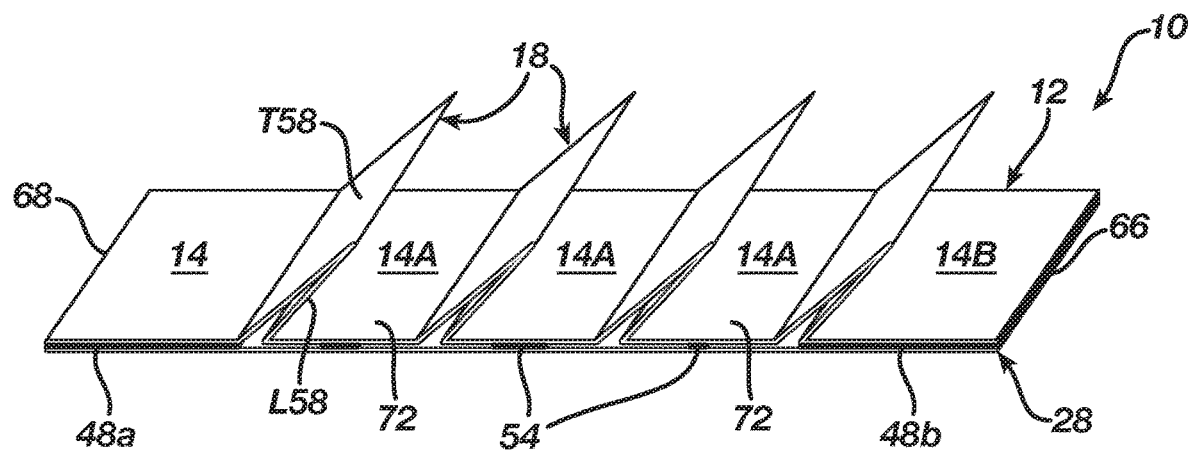
FIG. 11A shows a top perspective view of an exemplary embodiment of a dressing in accordance with the present invention.
Figure 11B:
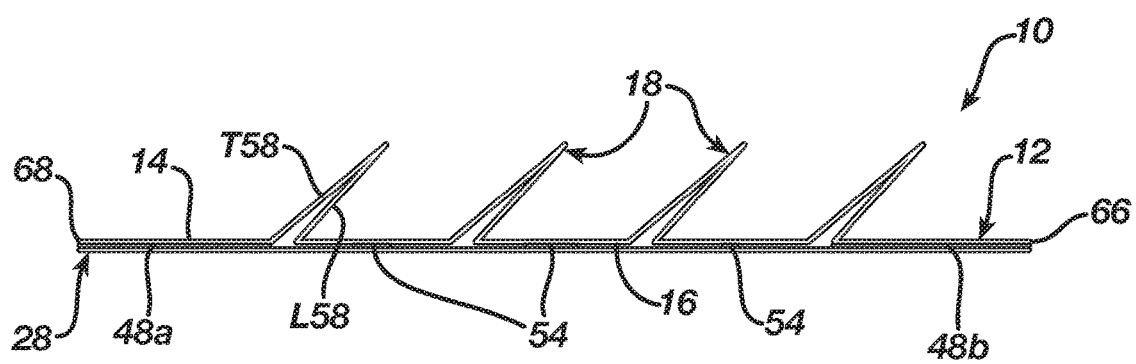
FIG. 11B shows a side view of the exemplary embodiment of the dressing illustrated in FIG. 11A.

In one embodiment, a dressing 10 comprises a layer of resilient material 12, as shown in FIGS. 10A and 10B, and an additional layer of material 28 to which the layer of resilient material 12 is adhered at discrete adhesive regions 54, 48a, and 48b. In one embodiment, the substantially fold-free segments 72 of the layer of resilient material 12, between neighboring pleats 18 and between pleats 18 and transverse edges 66 and 68, are adhesively adhered to the layer of additional material 28. Discrete adhesive regions 54, 48a, and 48b, spans the entire surface of a side of the substantially fold-free segments 72 (as shown in FIGS. 10A and 10B) or just a portion of the surface of a side of the substantially fold-free segments 72 (as shown in FIGS. 11A and 11B).

Figure 12A:
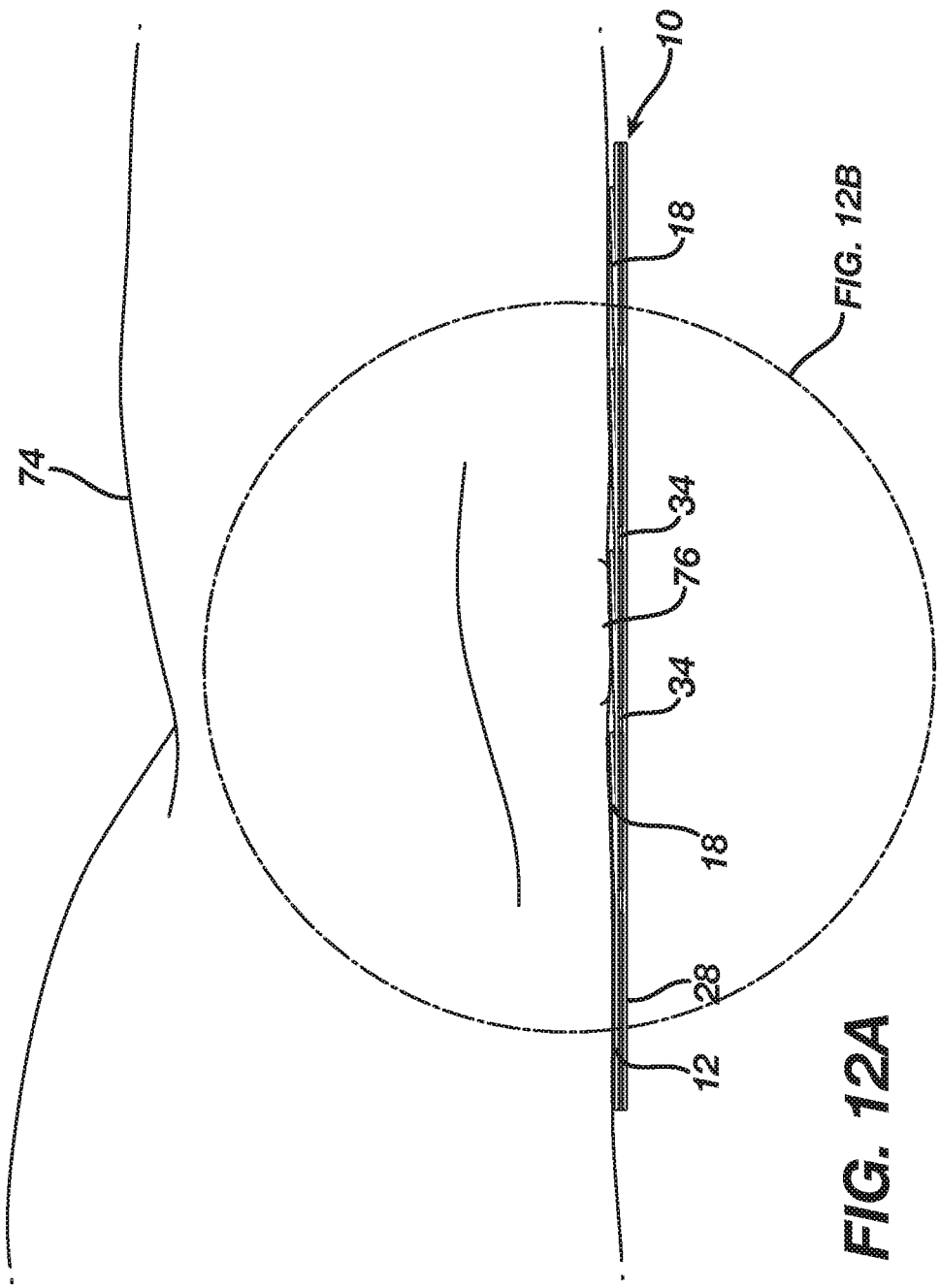
FIG. 12A shows a side view of an exemplary embodiment of a dressing in accordance with the present invention adhered to a skin surface at or near an extended elbow joint.
Figure 12B:
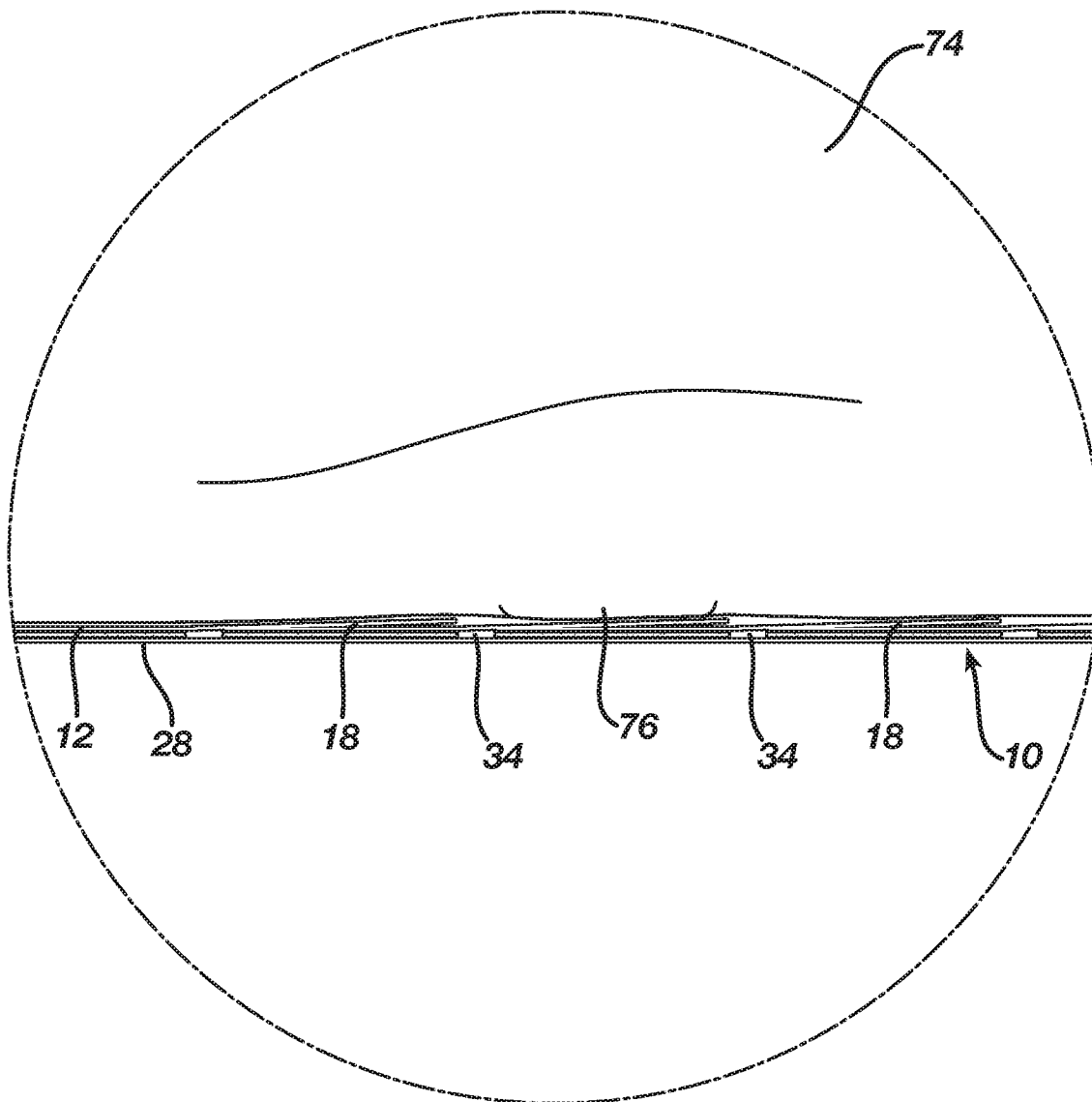
FIG. 12B shows a magnified side view of the exemplary embodiment of the dressing and extended elbow joint of FIG. 12A
Figure 12D:
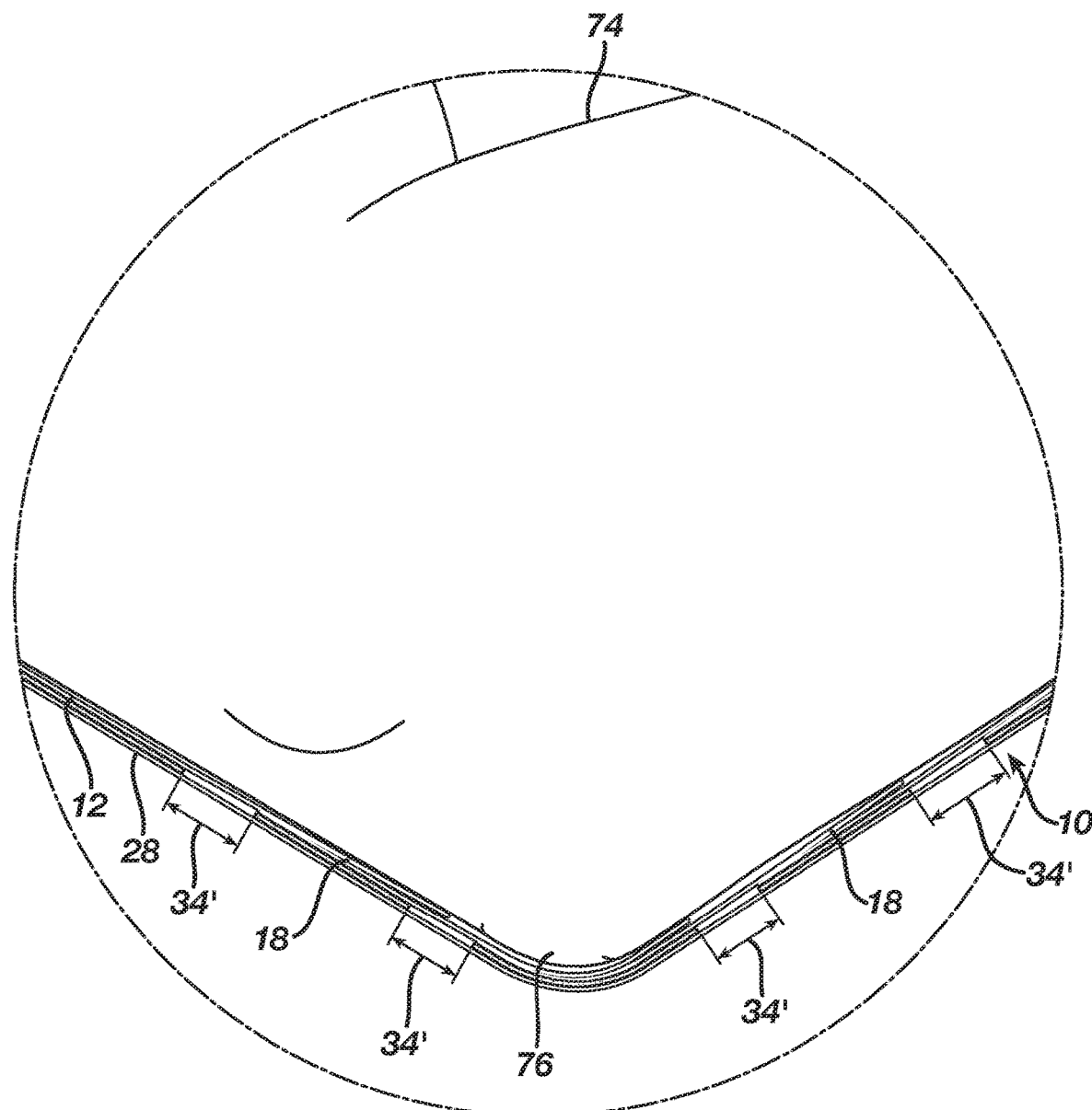
FIG. 12D shows a magnified side view of the exemplary embodiment of the dressing and flexed elbow joint of FIG. 12C.

In one embodiment of the dressing 10, as shown in FIG. 12A, when applied to a surface, such as a skin surface of an extended human forearm 74, each of the plurality of pleats 18 formed in the layer of resilient material 12 is forced to substantially overlay the substantially fold-free segment 72 between it (the pleat 18) and a neighboring pleat 18 or is forced to substantially overlay the substantially fold-free segment 72 between it (the pleat 18) and a transverse edge 66 or 68 of the layer of resilient material 12. In one embodiment of the dressing 10, as shown in FIGS. 12A and 12B, when applied to a surface of an articulated joint, such as a skin surface of a human elbow joint 76, each of the plurality of pleats 18 formed in the layer of resilient material 12 is forced to substantially overlay the substantially fold-free segment 72 between it (the pleat 18) and a neighboring pleat 18 or between it (the pleat 18) and a transverse edge 66 or 68 of the layer of resilient material 12 when the elbow joint 76 is extended. In one embodiment, as shown in FIGS. 10A-11B, each pleat 18 has a pair of side walls L58 and T58 arranged substantially in touching relationship near or at the open end 34 of the pleat 18. Similarly, as shown in FIG. 12A, wherein each pleat 18 is forced to substantially overlay a substantially fold-free segment 72 of the layer of resilient material 12 as a consequence of being pressed against a surface, such as a skin surface of an extended human forearm 74, each pair of side walls L58 and T58 of each pleat 18 is arranged substantially in touching relationship near or at the open end 34 of the pleat 18, thereby restricting the extent of the opening of the open end 34 of each pleat 18. In contrast, when the elbow joint 76 is flexed as in FIG. 12C, each of the plurality of pleats 18 remains substantially in an overlapping relation with an adjacent substantially fold-free segment 72 of the layer of resilient material 12, but each of the open ends 34 of the plurality of pleats 18 has an opening 34' that is greater in extent (e.g., wider apart) than the opening 34 of a pleat 18 in the embodiment of FIG. 12A. In one embodiment, as in FIGS. 12C and 12D, each pair of side walls L58 and T58 of each pleat 18 is spaced apart (in direction of arrows) to a greater extend at or near the open end 34 each of pleats 18 (as compared to their counterparts in the embodiment illustrated in FIGS. 12A and 12B) as a consequence of the additional layer of material 28 stretching to accommodate the elbow joint 76 in a flexed configuration. Without being limited by theory, it is believed that the presence of pleats 18 in the layer of resilient material 12 prevents or reduces any inhibitory or restrictive effect that the layer of resilient material 12 might exert, without such pleats, on the extensibility of the additional layer of material 28.

\Optional Components

Additional Layer of Material

In certain such embodiments, where additional layer material 28 acts as a backing layer, the material used in forming the additional layer 28 should be both conformable to the contours of the body and flexible so as to permit free movement of the body part wearing the product. In certain embodiments, it can be a woven or nonwoven fabric, a film or a foam. Polymeric materials useful in forming backing layers include polyolefin (such as polyethylene), polyurethane, and polyvinylchloride. Other examples of backings include, but are not limited to, nonwoven, woven, or knitted fabrics such as cotton, polyester, polyurethane, rayon and the like.

Polyethylene film may be optionally used to form additional layer of material 28 where additional layer of material 28 acts as a backing layer, and, in such instances, particularly effective results can be achieved with stretchable, elastomeric films formed of polyurethane, which has the further advantage of gas (including water vapor) transmissibility. It is to be understood, however, that, in such instances, other flexible, water insoluble polymeric films known in the art may be used. Furthermore, where additional layer of material 28 is used as a backing layer, additional layer of material 28 may be formed from closed-cell polymeric foam, particularly one with an integral skin covering the side of the closed-cell polymeric foam facing away from the skin of the user. In certain such embodiments, foam layers formed of polyurethane or polyethylenes are suitable, while other polymeric foams having similar properties may be used. In other embodiments, where additional layer of material 28 is used as a backing layer, additional layer of material 28 may be made from other polyolefins, vinyl polyethylene acetate, textile non-woven fabrics, rubber, or other materials known in the adhesive article art. In certain embodiments, polymers used to form additional layer of material 28 where additional layer of material 28 acts as a backing layer generally have viscosity of from about 500 to 500,000 centipoises at temperatures of about 190° C., or from about 1,000 to 30,000 centipoises at temperatures of about 190° C., or from about 3,000 to 15,000 centipoises at temperatures of about 190° C.

In certain embodiments, where additional layer of material 28 acts as a backing layer, additional layer of material 28 may be impermeable to liquid, but permeable to gas, which allows the wound and the skin to which the bandage and tape 10 of the present invention is adhered to breathe. In one embodiment, where additional layer of material 28 acts as a backing layer, additional layer of material 28 may have pores of such a size that will allow only the passage of gases, which have molecules of extremely small size.

Finally, where additional layer of material 28 acts as a backing layer, additional layer of material 28 may be perforated for still further ventilation of the skin. In certain such embodiments, perforations may be circular in area and have a range of diameters, such as from about 0.1 to about 0.8 millimeters. In certain other embodiments, however, where additional layer of material 28 acts as a backing layer, additional layer of material 28 may, when necessary, be totally impermeable to gases.

Adhesive

In some embodiments of the dressing 10, the layer of resilient material 12 further incorporates on at least one of the first (or skin facing) and second surfaces 14 and 16, an adhesive to provide adherence of the layer of resilient material 12 to the additional layer of material 28 and to a tissue/skin surface. When incorporated onto the layer of resilient material 12 of dressing 10, the adhesive is applied so as not restrict or inhibit the two or more folds 20 of the one or more pleats 18 from having a bias to return the length L of the layer of resilient material 12, after being extended to a second length L2, from the second length L2 to a first length L1, which is shorter than the second length L2. In general, any of a variety of pressure-sensitive adhesives can be used with the layer of resilient material 12 of the dressing 10. Exemplary pressure-sensitive adhesives, include pressure-sensitive adhesives that are biocompatible with human skin, including water soluble and water insoluble pressure-sensitive adhesives and pressure-sensitive adhesives that are dispersible in an aqueous environment. Examples of commercially available dispersible pressure-sensitive adhesive include: those sold under the trade name of HL-9415-X (available from H.B. Fuller Company). Another suitable adhesive includes about 10-75% by weight of a polyalkyloxazoline polymer, 10-75% by weight of a functional diluent comprising a hydroxy compound or a carboxylic acid compound, and 5-50% by weight of a tackifier. Thus, suitable pressure sensitive adhesive may vary in their compositions. Some may comprise hydrocolloids. The hydrocolloid element used may be any substance that has a good performance in this utilization, as for example, sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof, among others. Hydrocolloids, such as sodium carboxymethylcellulose and pectin, among others, are agents that form gels as soon as they come into contact with bodily fluids, from wounds, for example. When used in adhesive bandages, these hydrocolloids are combined with elastomers and/or adhesives. In certain embodiments, the layer of resilient material 12 comprising such hydrocolloids should provide a humid environment (but without saturation), which environment is a situation suitable for facilitating healing.

Other conventional adhesives known for such use in wound dressings may be used with the dressing 10 of the present invention. For example, pressure-sensitive acrylic adhesives, including those containing a resin for increasing adhesion, a cohesion increasing agent, an absorption agent (preferably a polyacrylate superabsorbent, a polyacrylate salt superabsorbent or a mixture thereof), and/or a plasticizer and optionally a pigment.

When applied to the layer of resilient material 12 of the dressing 10 of the present invention, the pressure-sensitive adhesive may be configured in discontinuous patterns, arranged in lines, screen, spray or any other configurations within the purview of a person skilled in the art.

In one embodiment, as shown in FIGS. 2A and 2B, a dressing 10 of the present invention, the adhesive is disposed on or contacts the second surface 16 of the layer of resilient material 12 in the form of one or more discrete adhesive regions 54 at discrete areas of the layer of resilient material 12. In one embodiment, dressing 10 further includes an additional layer of material 28, the additional layer of material 28 including a first surface 30 and an opposed second surface 32, wherein the first surface 30 of the additional layer of material 28 is adhered to the second surface 16 of the layer of resilient material 12 by the one or more discrete adhesive regions 54.

Figure 8A:
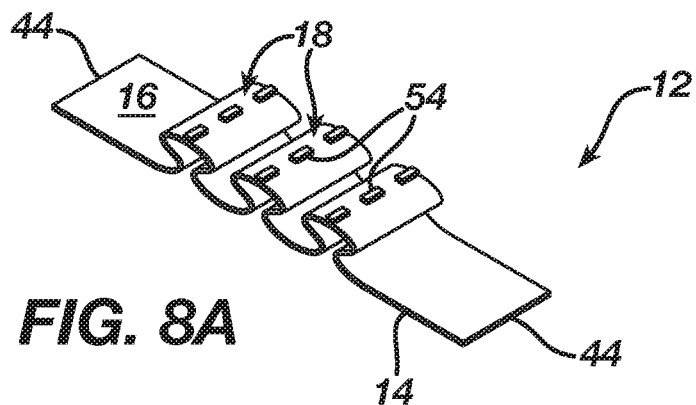
FIG. 8A shows a top perspective view of another exemplary embodiment of the layer of resilient material including pleats with rounded folds.
Figure 8B:
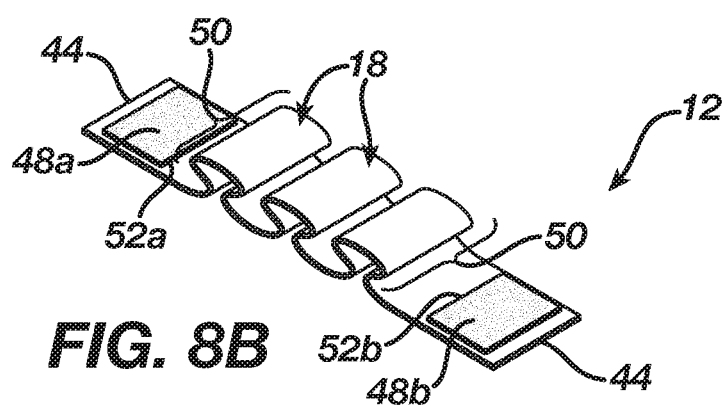
FIG. 8B shows a top perspective view of the exemplary embodiment of the layer of resilient material in FIG. 8A including discrete adhesive regions disposed proximate to each of the transverse edges of the layer of resilient material.
Figure 8C:
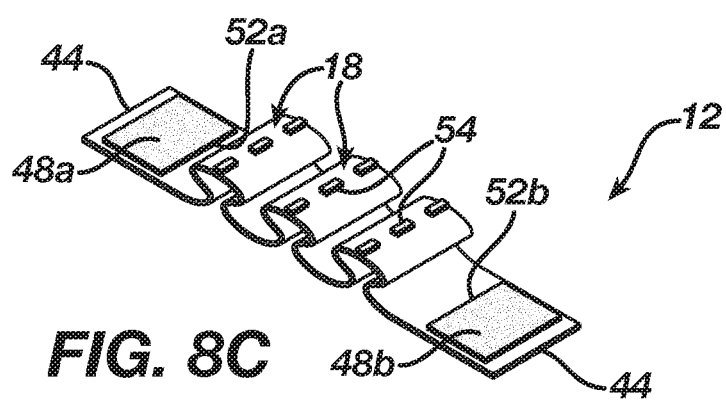
FIG. 8C shows a top perspective view of the exemplary embodiment of the layer of resilient material in FIG. 8A, further including a plurality discrete adhesive regions located on each of the pleats of the layer of resilient material.

In one embodiment, as shown in FIG. 8A, a dressing 10 of the present invention includes a plurality of discrete adhesive regions 54 disposed on the first and second surfaces 14 and 16 of the layer of resilient material 12 at discrete areas of the layer of resilient material 12. In one embodiment, as shown in FIG. 8C, a dressing 10 of the present invention not only includes a plurality of discrete adhesive regions 54 disposed on the first of the layer of resilient material 12, but also one or more discrete adhesive regions 48a and 48b disposed proximate a periphery 44 of the layer of resilient material 12. In one embodiment, as shown in FIG. 8B, the one or more discrete adhesive regions 48a and 48b disposed on the second surface 16 proximate a periphery 44 of the layer of resilient material 12 such that they form a pair of opposed adhesive regions spaced apart by an adhesive free-region 50, wherein the adhesive region 48a is located proximate the periphery 44 of the layer of resilient material 12 substantially parallel to the transverse centerline TC (not shown) and the adhesive region 48b is also located at the periphery 44 of the layer of resilient material 12 but substantially diametrically opposite the adhesive region 48a. In one embodiment, the layer of resilient material 12 of the dressing 10, includes the adhesive-free region 50 extending from an inner edge 52a of the adhesive region 48a to an inner edge 52b of the adhesive region 48b.

In one embodiment, as illustrated in FIGS. 2A to 2C, the dressing 10 further includes an additional layer of material 28, the additional layer of material 28 including a first surface 30 and an opposed second surface 32. In one embodiment, the additional layer of material 28 is adhered to the second surface 16 of the layer of resilient material 12 illustrated in FIGS. 8A to 8C at the first surface 30 of the additional layer of material 28 by a plurality of discrete adhesive regions, reference numeral 54 in FIG. 8A and/or reference numerals 48a and 48b in FIG. 8A in FIGS. 8B and 8C, to produce a dressing 10 in accordance with exemplary embodiments of the present invention. In one embodiment, such as illustrated in FIGS. 2B and 2C, a releasable release liner 56 may be added to the dressing 10 in accordance with the present invention. As shown in FIGS. 2A and 2B, release liner 56 is adapted to be releasably attached to the first surface 14 of the layer of resilient material 12, for example, by an adhesive. The release liner 56 can be releasably attached to the first surface 14 of the layer of resilient material 12 at continuous or discrete adhesive regions, for example reference numerals 54, 48a, and 48b, disposed on the first surface 14 of the layer of resilient material 12.

In one embodiment, as illustrated in FIGS. 2A, 2B and 2C, the dressing 10 further includes an additional layer of material 28, the additional layer of material 28 including a first surface 30 and an opposed second surface 32, wherein the additional layer of material 28 is adhered to the second surface 16 of the layer of resilient material 12 at discrete adhesive regions such as identified by reference numerals 54, 48a, and 48b in FIGS. 8B and 8C at the first surface 30 of the additional layer of material 28. When the additional layer of material 28 is adhered to the second surface 16 of the layer of resilient material 12 illustrated either in FIG. 8B, the first surface 30 of the additional layer of material 28 is adhered to the second surface 16 of the layer of resilient material 12 by the adhesive regions 48a and 48b. When the additional layer of material 28 is adhered to the second surface 16 of the layer of resilient material 12 illustrated either in FIG. 8C, the first surface 30 of the additional layer of material 28 is adhered to the second surface 16 of the layer of resilient material 12 by the adhesive regions 48a and 48b and by the plurality of discrete adhesive regions 54, as shown in exploded view in FIG. 2C.

Release Liner

In a further embodiment, as shown in FIG. 2C, the dressing 10 includes a release liner 56, the release liner 56 being in contact with, or which releasably contacts, the first surface 14 of the layer of resilient material 12 and/or, in releasably contacts the first surface 30 of the additional layer of material 28. In certain embodiments, the release liner 56 and additional layer of material 28 are sized to extend beyond the periphery of the layer of resilient material 12 in at least one, or in one of more directions. The release liner 56 can be releasably attached to the first surface 14 of the layer of resilient material 12 by a continuous or discrete adhesive regions disposed on the first surface 14 of the layer of resilient material 12. In one embodiment, the release liner 56 includes a first surface 60 and a second surface 58, wherein the first surface 60 of the release liner 56 is releasably adhered to the first surface 14 of the layer of resilient material 12 by an adhesive disposed on the first surface 14 of the layer of resilient material 12.

In one embodiment, as shown in FIG. 2A, a dressing 10 includes of a layer of resilient material 12 which includes a plurality of discrete adhesive regions 54 disposed on the first and second surfaces 14 and 16 of the layer of resilient material 12 at discrete areas of the layer of resilient material 12, the dressing 10 further includes an additional layer of material 28 and a release liner 56, the additional layer of material 28 including a first surface 30 and an opposed second surface 32, and the release liner 56 including a first surface 58 and a second surface 60, wherein the first surface 30 of the additional layer of material 28 is adhered to the second surface 16 of the layer of resilient material 12 by the plurality of discrete adhesive regions 54, and the second surface 60 of the release liner 56 is releasably adhered to the first surface 14 of the layer of resilient material 12 by the plurality of discrete adhesive regions 54 disposed on the first surface 14 of the layer of resilient material 12.

The releasable liner 56 can be comprised of any suitable material, including, for example, polyethylene, polypropylene, kraft papers, polyester, polystyrene (PS), high impact polystyrene (HIPS) or composites of any of these materials.

Although specific embodiments of this invention have been shown and described herein, it is understood that these embodiments are merely illustrative of the many possible specific arrangements that can be devised in application of the principles of the invention. Numerous and varied other arrangements can be devised in accordance with these principles by those of ordinary skill in the art without departing from the spirit and scope of the invention. Thus, the scope of the present invention should not be limited to the structures described in this application, but only by the structures described by the language of the claims and the equivalents of those structures.

Embodiments of the Present Invention

1. A dressing comprising a layer of resilient material, the layer of resilient material having a length direction (LD) and a width direction (WD), which together define a horizontal plane (HP), the horizontal plane HP having a first surface and a second opposed surface, a longitudinal centerline (LC) and a transverse centerline (TC), the layer of resilient material further including one or more pleats formed in at least a portion thereof, each pleat comprising two or more folds, at least one of which folds each pleat shares in common with a neighboring pleat when there are two or more pleats, each pleat further has a length extending in a direction taken along the pleat length, a pleat width, and a lengthwise centerline (PC) bisecting the pleat width, wherein the direction of each pleat length independently makes an angle with the longitudinal centerline LC in the horizontal plane HP, and wherein the angle φ has a value that falls within a range specified by the equation: $0°<\varphi<180°$.

2. The dressing of embodiment 1, wherein the lengthwise centerlines PC of a pleat is oriented substantially parallel relative to the lengthwise centerlines PC of an adjacent pleat.

3. The dressing of embodiment 1, wherein the lengthwise centerline PC of one or more pleats is oriented at angle φ with respect to the longitudinal centerline LC such that angle φ has a value that falls within a range specified by the equation: $0°<\varphi\leq 90°$.

4. The dressing of embodiment 1, wherein the lengthwise centerline PC of one or more pleats is oriented at angle φ with respect to the longitudinal centerline LC such that angle φ has a value that falls within a range specified by the equation: $90°<\varphi<180°$.

5. The dressing of any of the previous embodiments or combinations thereof, wherein the longitudinal centerline LC divides the width of the layer of resilient material in two substantially equal halves.

6. The dressing of any of the previous embodiments or combinations thereof, wherein the transverse centerline TC divides the length L of the layer of resilient material in two substantially equal halves.

7. The dressing of any of the previous embodiments or combinations thereof, wherein the two or more folds in a pleat are incorporated to form an open end and a closed end.

8. The dressing of embodiment 7 (or, any of the previous embodiments or combinations thereof), wherein the open end and the closed end of a pleat are spaced from one another by a pair of side walls extending from the closed end to the open end of the pleat and wherein the pleat is axially oriented substantially orthogonal to the horizontal plane HP.

9. The dressing of any of embodiments 1-6 or combinations thereof (or, any of the previous embodiments or combinations thereof), wherein the two or more folds in each of the one or more pleats are arranged such that each pleat has an open end and a closed end spaced from the open end by a pair of side walls extending from the closed end to the open end of the pleat and wherein the pleat is axially oriented at an angle β to the horizontal plane HP, wherein the angle β has a value that falls within a range specified by the equation: $0° < \beta \leq 180°$.

10. The dressing of any of embodiments 1-6 or combinations thereof (or, any of the previous embodiments or combinations thereof), wherein the two or more folds in each of the one or more pleats are arranged such that each pleat has an open end and a closed end spaced from the open end by a pair of side walls extending from the closed end to the open end of the pleat and wherein the pleat is axially oriented at an angle β to the horizontal plane HP, wherein the angle β has a value that falls within a range specified by the equation: $90° \leq \beta \leq 180°$.

11. The dressing of any of embodiments 7-10 or combinations thereof (or, any of the previous embodiments or combinations thereof), wherein the two or more pleats having their open ends facing in alternately opposite directions with respect to the first surface and the second surface of the layer of resilient material.

12. The dressing of any of the previous embodiments or combinations thereof, wherein at least one of the one or more pleats has folds incorporated so as to form a pair of adjacent closed ends, spaced apart by a substantially fold-free segment of the layer of resilient material.

13. The dressing of embodiment 11 (or, any of the previous embodiments or combinations thereof), wherein each of the substantially fold-free segments of the layer of resilient material of the pleats has an inner surface and an outer surface, and wherein the substantially fold-free segments of the layer of resilient materials of the pleats are arranged such that the inner surface of a substantially fold-free segment of the layer of resilient material of any pleat faces in a direction opposite to the direction of an inner surface of a substantially fold-free segment of the layer of resilient material of an adjacent pleat.

14. The dressing of any of embodiments 1-9 and 11, or combinations thereof (or, any of the previous embodiments or combinations thereof), wherein the two or more folds are rounded folds.

15. The dressing of any of embodiments 1-13, or combinations thereof (or, any of the previous embodiments or combinations thereof), wherein the two or more folds are creased folds.

16. The dressing of any of the previous embodiments or combinations thereof, wherein the length L of the layer of resilient material is greater than its width W.

17. The dressing of any of the previous embodiments or combinations thereof, wherein the length L and the width W of the layer of resilient material are substantially equal.

18. The dressing of any of the previous embodiments or combinations thereof further including an additional layer of material adhered to at least a portion of the second surface of the layer of resilient material.

19. The dressing of any of the previous embodiments or combinations thereof, wherein the layer of resilient material further includes a first transverse periphery and a second opposed transverse periphery, a first and second discrete adhesive regions disposed on the second surface of the layer of resilient material respectively proximate each of the first and second transverse peripheries of the layer of resilient material, wherein the first and second discrete adhesive regions are spaced apart by a substantially adhesive free-region.

20. The dressing of embodiment 19 (or, any of the previous embodiments or combinations thereof), wherein the first discrete adhesive region and the second discrete adhesive region are substantially free of pleats.

21. The dressing of any of embodiments 12 and 20, or combinations thereof (or, any of the previous embodiments or combinations thereof), wherein the one or more pleats are located in an adhesive-free region of the layer of resilient material.

22. The dressing of any of the previous embodiments or combinations thereof, wherein the length L of the layer of resilient material is extendable between a first length L1 and a second length L2 longer than the first length L1.

23. The dressing of any of the previous embodiments or combinations thereof, wherein the two or more folds of each pleat are biased to return the length L of the layer of resilient material, after being extended to the second length L2, from the second length L2 to the first length L1.

24. A dressing comprising a layer of resilient material, the layer of resilient material having:

(a) a length direction (LD) and a width direction (WD), which together define a horizontal plane (HP), the horizontal plane HP having a first surface and a second opposed surface, a longitudinal centerline (LC) and a transverse centerline (TC);

(b) one or more pleats formed in at least a portion of the layer of resilient material, each pleat comprising two or more folds, at least one of which folds each pleat shares in common with a neighboring pleat, each pleat further has a pleat length extending in a pleat direction, a pleat width, and a lengthwise centerline (PC) bisecting the pleat width, wherein each pleat direction of a pleat length independently makes an angle φ with the longitudinal centerline LC in the horizontal plane HP, and wherein the angle φ has a value that falls within a range specified by the equation: $0° < \varphi < 180'$;

(c) a plurality of discrete adhesive regions disposed on the second surface of the layer of resilient material at discrete areas of the layer of resilient material; and (d) an additional layer of material having a first surface and a second opposed surface, the first surface of the additional layer of material adhered to the second surface of the layer of resilient material by the plurality of discrete adhesive regions.

25. The dressing of any of the previous embodiments or combinations thereof, further including a release liner covering the first surface of the layer of resilient material.

26. The dressing of embodiment 25 (or, any of the previous embodiments or combinations thereof), wherein the release liner includes a first surface and an opposed second surface, the second surface of the release liner being releasably adhered to the first surface of the layer of resilient material.

27. A dressing comprising a layer of resilient material, the layer of resilient material having:

(i) a first longitudinal edge and a second longitudinal edge, which together define a width (W) of the layer of resilient material;

(ii) a first transverse edge and a second transverse edge, which together define a length (L) of the layer of resilient material, the length L and width W of the layer of resilient material 12 having a length direction (LD) and a width direction (WD) respectively, the length direction LD and the width direction WD together defining a horizontal plane (HP), the horizontal plane HP having a first surface and a second opposed surface, a longitudinal centerline (LC), and a transverse centerline (TC); and (iii) a plurality of pleats formed in at least a portion of the layer of resilient material, each pleat comprising a multiplicity of folds, each fold extending from the first longitudinal edge to the second longitudinal edge, each pleat having a closed end (or an apex) 36 defined by a fold, an open end spaced from and opposite the closed end (or apex), and a trailing side wall and an opposing leading side wall sharing a common transverse edge running along the fold of the closed end (the apex) of the pleat, each of the trailing and leading side walls of the pleat further has a second transverse edge spaced from and opposite the common transverse edge and disposed on opposite sides of the open end of the pleat, wherein at least two (adjacent) neighboring pleats are arranged in a spaced relation to each other with a substantially fold-free segment of the layer of resilient material spanning the distance from the second transverse edge of the leading side wall of one of the pleats to the second transverse edge of the trailing sidewall of the neighboring pleat.

28. The dressing of embodiment 27 (or, any of the previous embodiments or combinations thereof), wherein the length L of the layer of resilient material is extendable between a first length L1 and a second length L2 longer than the first length L1.

29. The dressing of embodiment 28 (or, any of the previous embodiments or combinations thereof), wherein the multiplicity of folds of each pleat are biased to return the length L of the layer of resilient material, after being extended to the second length L2, from the second length L2 to the first length L1.

30. The dressing of any of the previous embodiments or combinations thereof, wherein any pleat is arranged in a spaced relation with a neighboring pleat such that a substantially fold-free segment of the layer of resilient material spans the distance from the second transverse edge of the leading side wall of one of pleat to the second transverse edge of the trailing sidewall of a neighboring pleat.

31. The dressing of any of the previous embodiments or combinations thereof, wherein at least one pleat is movable between collapsed and upright configurations, where in the collapsed configuration the at least one pleat is in an overlaying relationship with the substantially fold-free segment of the layer of resilient material spanning the distance between it and its neighbor (an adjacent pleat), where in the upright configuration the at least one pleat is in a substantially upright orientation relative to the substantially fold-free segment of the layer of resilient as a consequence of being moved by the application of an external force to the layer of resilient material, and wherein the at least one pleat is biased to return to the collapsed configuration when the external force is removed.

32. The dressing of any of the previous embodiments or combinations thereof, wherein the plurality of pleats are movable between collapsed and upright configurations, where:

(a) in the collapsed configuration, each of the plurality of pleats is succeeded by a neighboring pleat is in an overlaying relationship with the substantially fold-free segment of the layer of resilient material spanning the distance between it and the succeeding neighbor (an adjacent pleat), and (b) in the upright configuration the plurality of pleats is in a substantially upright orientation relative to the substantially fold-free segment of the layer of resilient as a consequence of being moved by the application of an external force to the layer of resilient material, and wherein the plurality of pleats is biased to return to the collapsed configuration when the external force is removed.

33. The dressing of any of the previous embodiments or combinations thereof, wherein each pleat has a length, a direction, and a lengthwise centerline (PC) extending in a pleat direction, wherein the pleat direction makes an angle $\varphi$ with the longitudinal centerline LC in the horizontal plane HP, wherein the angle $\varphi$ has a value that falls within a range specified by the equation: $0° < \varphi < 180°$.

34. The dressing of embodiment 33 (or, any of the previous embodiments or combinations thereof), wherein the angle $\varphi$ has a value that falls within a range specified by the equation: $0° < \varphi \leq 90°$.

35. The dressing of embodiment 33 (or, any of the previous embodiments or combinations thereof), wherein the angle $\varphi$ has a value that falls within a range specified by the equation: $90° \leq \varphi < 180°$.

36. A dressing comprising a layer of resilient material, the layer of resilient material having a length direction (LD) and a width direction (WD), which together define a horizontal plane (HP), the horizontal plane HP having a first surface and a second opposed surface, a longitudinal centerline (LC) and a transverse centerline (TC), the layer of resilient material further including one or more pleats formed in at least a portion thereof, each pleat comprising two or more folds, at least one of which folds each pleat shares in common with a neighboring pleat when there are two or more pleats, each pleat further has a length extending in a direction taken along the pleat length, a pleat width, and a lengthwise centerline (PC) bisecting the pleat width, each pleat includes two or more folds incorporated so as to form an open end and a closed end, with a pair of side walls of the pleat, each side wall extending between a fold contributing to formation of the open end and the closed end, wherein one or more pleats has a pair of adjacent closed ends, spaced apart by a substantially fold-free segment of the layer of resilient material, and wherein the direction of each pleat length independently makes an angle $\varphi$ with the longitudinal centerline LC in the horizontal plane HP, and wherein the angle $\varphi$ has a value that falls within a range specified by the equation: $0° < \varphi < 180°$.

37. The dressing of embodiment 36 (or, any of the previous embodiments or combinations thereof), wherein the lengthwise centerlines PC of a pleat is oriented substantially parallel relative to the lengthwise centerlines PC of an adjacent pleat.

38. The dressing of embodiment 36 (or, any of the previous embodiments or combinations thereof), wherein the lengthwise centerline PC of one or more pleats is oriented at angle $\varphi$ with respect to the longitudinal centerline LC such that angle $\varphi$ has a value that falls within a range specified by the equation: $0° < \varphi \leq 90°$.

39. The dressing of embodiment 36 (or, any of the previous embodiments or combinations thereof), wherein the lengthwise centerline PC of one or more pleats is oriented at angle φ with respect to the longitudinal centerline LC such that angle φ has a value that falls within a range specified by the equation: 90°<φ<180°.

40. The dressing of any of embodiments 36-39 or combinations thereof, wherein the two or more pleats have their open ends facing in alternately opposite directions with respect to the first surface and the second surface of the layer of resilient material.

41. The dressing of any of embodiments 36-40 or combinations thereof, wherein each of the substantially fold-free segments of the layer of resilient material has an inner surface and an outer surface, and wherein the substantially fold-free segments of the layer of resilient material are arranged such that the inner surface of a substantially fold-free segment of the layer of resilient material of any pleat faces in a direction opposite to the direction of an inner surface of a substantially fold-free segment of the layer of resilient material of an adjacent pleat.

42. The dressing of any of embodiments 36-41, or combinations thereof, wherein the two or more folds of each pleat are creased folds.

The dressing of any of the previous embodiments or combinations thereof, wherein the length L of the layer of resilient material is greater than its width W.

43. The dressing of any of the previous embodiments or combinations thereof, wherein the length L and the width W of the layer of resilient material are substantially equal.

44. The dressing of any of the previous embodiments or combinations thereof further including an additional layer of material adhered to at least a portion of the second surface of the layer of resilient material.

45. The dressing of any of the previous embodiments or combinations thereof, wherein the layer of resilient material further includes a first transverse periphery and a second opposed transverse periphery, a first and second discrete adhesive regions disposed on the second surface of the layer of resilient material respectively proximate each of the first and second transverse peripheries of the layer of resilient material, wherein the first and second discrete adhesive regions are spaced apart by a substantially adhesive free-region.

46. The dressing of embodiment 45 (or, any of the previous embodiments or combinations thereof), wherein the first discrete adhesive region and the second discrete adhesive region are substantially free of pleats.

47. The dressing of any of embodiments 36-46, or combinations thereof, wherein the one or more pleats are located in an adhesive-free region of the layer of resilient material.

48. The dressing of any of embodiments 36-47, or combinations thereof, wherein the length L of the layer of resilient material is extendable between a first length L1 and a second length L2 longer than the first length L1.

49. The dressing of any embodiments 36-48, or combinations thereof, wherein the two or more folds of each pleat are biased to return the length L of the layer of resilient material, after being extended to the second length L2, from the second length L2 to the first length L1.

What is claimed is:

1. A dressing comprising a layer of resilient material, the layer of resilient material having a length direction (LD) and a width direction (WD), which together define a horizontal plane (HP), the layer of resilient material having a first surface and a second opposed surface, a longitudinal centerline (LC) and a transverse centerline (TC), the layer of resilient material further including one or more pleats formed in at least a portion thereof, each pleat comprising two or more folds, at least one of which folds each pleat shares in common with a neighboring pleat when there are two or more pleats, each pleat further has (i) length extending in a direction taken along a pleat length, (ii) a pleat width, and (iii) a lengthwise centerline (PC) bisecting the pleat width, wherein the direction of each pleat length independently makes an angle φ with the longitudinal centerline LC in the horizontal plane HP, and wherein the angle φ has a value that falls within a range specified by the equation: 0°<φ<180°, wherein at least one pleat is movable between collapsed and upright configurations, wherein the collapsed configuration the at least one pleat is in an overlaying relationship with the substantially fold-free segment of the layer of resilient material spanning the distance between it and its neighbor (an adjacent pleat), where in the upright configuration the at least one pleat is in a substantially upright orientation relative to the substantially fold-free segment of the layer of resilient as a consequence of being moved by the application of an external force to the layer of resilient material, and wherein the at least one pleat is biased to return to the collapsed configuration when the external force is removed.

2. The dressing of claim 1, wherein the lengthwise centerline PC of a pleat is oriented substantially parallel relative to the lengthwise centerline PC of an adjacent pleat.

3. The dressing of claim 1, wherein the lengthwise centerline PC of one or more pleats is oriented at angle φ with respect to the longitudinal centerline LC such that angle φ has a value that falls within a range specified by the equation: 0°<φ≤90°.

4. The dressing of claim 1, wherein the lengthwise centerline PC of one or more pleats is oriented at angle φ with respect to the longitudinal centerline LC such that angle φ has a value that falls within a range specified by the equation: 90°<φ<180°.

5. The dressing of claim 1, wherein the longitudinal centerline LC divides the width of the layer of resilient material in two substantially equal halves.

6. The dressing of claim 1, wherein the transverse centerline TC divides the length L of the layer of resilient material in two substantially equal halves.

7. The dressing of claim 1, wherein the two or more folds in a pleat are incorporated to form an open end and a closed end.

8. The dressing of claim 7, wherein the open end and the closed end of a pleat are spaced from one another by a pair of side walls extending from the closed end to the open end of the pleat and wherein the pleat is axially oriented substantially orthogonal to the horizontal plane HP.

9. The dressing of claim 7, wherein the two or more folds in each of the one or more pleats are arranged such that each pleat has an open end and a closed end spaced from the open end by a pair of side walls extending from the closed end to the open end of the pleat and wherein the pleat is axially oriented at an angle β to the horizontal plane HP, wherein the angle β has a value that falls within a range specified by the equation: 0°<β≤180°.

10. The dressing of claim 9, wherein the two or more folds in each of the one or more pleats are arranged such that each pleat has an open end and a closed end spaced from the open end by a pair of side walls extending from the closed end to the open end of the pleat and wherein the pleat is axially oriented at an angle β to the horizontal plane HP, wherein the angle β has a value that falls within a range specified by the equation: 90° β≤180°.

11. The dressing of claim 7, wherein the two or more pleats having their open ends facing in alternately opposite directions with respect to the first surface and the second surface of the layer of resilient material.

12. The dressing of claim 11, wherein each of the substantially fold-free segments of the layer of resilient material of the pleats has an inner surface and an outer surface, and wherein the substantially fold-free segments of the layer of resilient materials of the pleats are arranged such that the inner surface of a substantially fold-free segment of the layer of resilient material of any pleat faces in a direction opposite to the direction of an inner surface of a substantially fold-free segment of the layer of resilient material of an adjacent pleat.

13. The dressing of claim 1, further including an additional layer of material adhered to at least a portion of the second surface of the layer of resilient material.

14. The dressing of claim 1, wherein the layer of resilient material further includes a first transverse periphery and a second opposed transverse periphery, a first and second discrete adhesive regions disposed on the second surface of the layer of resilient material respectively proximate each of the first and second transverse peripheries of the layer of resilient material, wherein the first and second discrete adhesive regions are spaced apart by a substantially adhesive free-region.

15. The dressing of claim 14, wherein the first discrete adhesive region and the second discrete adhesive region are substantially free of pleats.

16. The dressing of claim 14, wherein the one or more pleats are located in a substantially adhesive-free region of the layer of resilient material.

17. The dressing of claim 1, wherein the length L of the layer of resilient material is extendable between a first length L1 and a second length L2 longer than the first length L1.

18. The dressing of claim 17, wherein the two or more folds of each pleat are biased to return the length L of the layer of resilient material, after being extended to the second length L2, from the second length L2 to the first length L1.

19. A dressing comprising a layer of resilient material, the layer of resilient material having:
(i) a first longitudinal edge and a second longitudinal edge, which together define a width (W) of the layer of resilient material;
(ii) a first transverse edge and a second transverse edge, which together define a length (L) of the layer of resilient material, the length L and width W of the layer of resilient material 12 having a length direction (LD) and a width direction (WD) respectively, the length direction LD and the width direction WD together defining a horizontal plane (HP), the layer of resilient material having a first surface and a second opposed surface, a longitudinal centerline (LC), and a transverse centerline (TC); and
(iii) a plurality of pleats formed in at least a portion of the layer of resilient material, each pleat comprising a multiplicity of folds, each fold extending from the first longitudinal edge to the second longitudinal edge, each pleat having a closed end (or an apex) 36 defined by a fold, an open end spaced from and opposite the closed end (or apex), and a trailing side wall and an opposing leading side wall sharing a common transverse edge running along the fold of the closed end (the apex) of the pleat, each of the trailing and leading side walls of the pleat further has a second transverse edge spaced from and opposite the common transverse edge and disposed on opposite sides of the open end of the pleat, wherein at least two (adjacent) neighboring pleats are arranged in a spaced relation to each other with a substantially fold-free segment of the layer of resilient material spanning the distance from the second transverse edge of the leading side wall of one of the pleats to the second transverse edge of the trailing sidewall of the neighboring pleat, and at least one pleat is movable between collapsed and upright configurations, wherein the collapsed configuration the at least one pleat is in an overlaying relationship with the substantially fold-free segment of the layer of resilient material spanning the distance between it and its neighbor (an adjacent pleat), where in the upright configuration the at least one pleat is in a substantially upright orientation relative to the substantially fold-free segment of the layer of resilient as a consequence of being moved by the application of an external force to the layer of resilient material, and wherein the at least one pleat is biased to return to the collapsed configuration when the external force is removed.

* * * * *